(12) United States Patent
Maikap et al.

(10) Patent No.: US 7,235,647 B2
(45) Date of Patent: Jun. 26, 2007

(54) INTERMEDIATE AND PROCESS FOR PREPARING OF β- ANOMER ENRICHED 2¹-DEOXY,2¹,2¹-DIFLUORO-D-RIBOFURANOSYL NUCLEOSIDES

(75) Inventors: Golak Chandra Maikap, Uttar Pradesh (IN); Deependra Bhatt, Uttar Pradesh (IN); Bijan Kumar Panda, Uttar Pradesh (IN)

(73) Assignee: Dabur Pharma Limited, New Delhi (IN)

( * ) Notice: Subject to any disclaimer, the term of this patent is extended or adjusted under 35 U.S.C. 154(b) by 24 days.

(21) Appl. No.: 11/332,830

(22) Filed: Jan. 13, 2006

(65) Prior Publication Data

US 2006/0217547 A1 Sep. 28, 2006

(30) Foreign Application Priority Data

Mar. 4, 2005 (IN) .......................... 472/DEL/2005

(51) Int. Cl.
C07H 5/04 (2006.01)
C07H 5/06 (2006.01)
C07H 19/00 (2006.01)

(52) U.S. Cl. ............................. 536/18.7; 536/217.11; 536/28.5; 536/55.3

(58) Field of Classification Search ............... 536/18.7, 536/27.11, 28.5, 55.3
See application file for complete search history.

(56) References Cited

U.S. PATENT DOCUMENTS

| | | | | |
|---|---|---|---|---|
| 4,526,988 A | * | 7/1985 | Hertel | 549/313 |
| 4,692,434 A | * | 9/1987 | Hertel | 514/49 |
| 4,814,438 A | * | 3/1989 | Armour et al. | 536/27.23 |
| 4,994,558 A | * | 2/1991 | Armour et al. | 530/391.9 |
| 5,061,793 A | * | 10/1991 | Grindey et al. | 536/27.14 |
| 5,118,820 A | * | 6/1992 | Hertel | 549/313 |
| 5,223,608 A | | 6/1993 | Chou et al. | |
| 5,256,798 A | | 10/1993 | Chou et al. | |
| 5,371,210 A | * | 12/1994 | Chou | 536/27.11 |
| 5,401,838 A | * | 3/1995 | Chou | 536/28.1 |
| 5,401,861 A | | 3/1995 | Chou | |
| 5,420,266 A | * | 5/1995 | Britton et al. | 536/28.52 |
| 5,426,183 A | * | 6/1995 | Kjell | 536/28.55 |
| 5,430,026 A | * | 7/1995 | Hertel et al. | 514/43 |
| 5,464,826 A | * | 11/1995 | Grindey et al. | 514/50 |
| 5,521,294 A | * | 5/1996 | Wildfeuer | 536/18.7 |
| 5,559,222 A | * | 9/1996 | Wirth | 536/28.5 |
| 5,574,021 A | * | 11/1996 | Hertel et al. | 514/45 |
| 5,594,124 A | * | 1/1997 | Chou | 536/28.4 |
| 5,606,048 A | * | 2/1997 | Chou et al. | 536/27.11 |
| 5,608,043 A | * | 3/1997 | Wirth | 536/4.1 |
| 5,637,688 A | * | 6/1997 | Berglund | 536/28.5 |
| 5,644,043 A | * | 7/1997 | Hertel et al. | 536/18.4 |
| 5,648,473 A | * | 7/1997 | Chou | 536/18.4 |
| 5,744,597 A | * | 4/1998 | Chou et al. | 536/55.3 |
| 5,808,048 A | * | 9/1998 | Berglund | 536/28.5 |
| 5,821,357 A | * | 10/1998 | Chou et al. | 536/55.3 |

FOREIGN PATENT DOCUMENTS

| | | |
|---|---|---|
| EP | 577303 A1 | 1/1994 |
| WO | WO2006/071090 A1 * | 7/2006 |
| WO | WO2006/092808 A1 * | 9/2006 |

OTHER PUBLICATIONS

Hertel et al., "Synthesis of 2-Deoxy-2,2-difluoro-D-ribose and 2-Deoxy-2,2-difluoro-D-ribofuranosyl Nucleosides," Journal of Organic Chemistry, 53(11), 2406-2409 (1988).*

Schmidt et al., "New Methods fo the Synthesis of Glycosides and Oligosaccharides. Are There Alternatives to the Koenigs-Knorr Method?" Angewandte Chemie, International Edition, 25(3), 212-235 (1986).*

Shohda et al., "Detailed Studies on Trimethylsilyl Triflate Mediated Glycosylation Via a 3,5-O-(1, 1, 3, 3-Tetraisopropyldisiloxane-1,3-diyl)-2-O-methylribofuranosyl Trichloroacetimidate Intermediate," Nucleosides & Nucleotides, 17(12), 2199-2210 (1998).*

"Search Report for International Application No. PCTIN2005/000322", (May 1, 2006), 3 pgs.

* cited by examiner

*Primary Examiner*—L. E. Crane
(74) *Attorney, Agent, or Firm*—Schwegman, Lundberg, Woessner and Kluth P.A.

(57) ABSTRACT

The present invention provides a highly stereoselective, simple and economical glycosylation process for preparation of β-anomer enriched $2^1$-deoxy-$2^1$,$2^1$-D-ribofuranosyl difluoronucleosides of formula (II), and physiologically acceptable slats thereof, in particular, the β-enriched anomer of gemcitabine hydrochloride of formula (IIb) in purity of >99% is provided through utilization of a novel trichloroacetimidate of formula (I).

20 Claims, No Drawings

INTERMEDIATE AND PROCESS FOR PREPARING OF β- ANOMER ENRICHED 2¹-DEOXY,2¹,2¹-DIFLUORO-D-RIBOFURANOSYL NUCLEOSIDES

RELATED APPLICATION

This application claims priority under 35 U.S.C. 119 to Indian Application No. 472/DEL/2005, filed Mar. 4, 2005, which application is incorporated herein by reference in its entirety and made a part hereof.

FIELD OF THE INVENTION

The present invention relates to a novel intermediate of formula (I), a process for preparation thereof and its use in the preparation of β-enriched anomers of therapeutically and commercially valuable $2^1$-deoxy-$2^1,2^1$-D-ribofuranosyl difluoronucleosides of formula (II), and physiologically acceptable salts thereof. In particular, the present invention relates to a selective process for manufacture of the β-enriched anomer of gemcitabine hydrochloride of formula (IIb) in high purity.

BACKGROUND OF THE INVENTION $2^1$-deoxy-$2^1,2^1$-D-ribofuranosyl difluoronucleosides of formula (II),

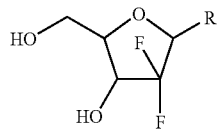

wherein the group R represents a base selected from a pyrimidine or purine derivative and P represents hydrogen or a hydroxy protective group possess useful therapeutic properties and one such $2^1$-deoxy-$2^1,2^1$-D-ribofuranosyl difluoronucleoside of therapeutic and commercial importance is gemcitabine hydrochloride of formula (IIb), first disclosed by Hertel et al. in U.S. Pat. No. 4,526,988; its continuation-in-part U.S. Pat. No. 4,692,434 and divisional, U.S. Pat. No. 4,808,614 as an useful antiviral and later by Grindey et al. in U.S. Pat. No. 5,464,826 as an useful anti-tumour agent for treatment of susceptible neoplasms in mammals.

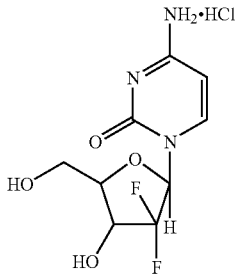

U.S. Pat. Nos. 4,526,988, 4,692,434 and 4,808,614 disclose a method for synthesis of the $2^1$-deoxy-$2^1,2^1$-D-ribofuranosyl difluoronucleosides of formula (II) including gemcitabine hydrochloride of formula (IIb) comprising hydrolysis of an alkyl-3-dioxolanyl-2,2-difluoro-3-hydroxypropionate (1) to give a lactone (III), which after suitable protection of the hydroxyl groups is reduced to give the protected $2^1$-deoxy-$2^1,2^1$-difluororibose of formula (IV). The free hydroxy group of compound (IV) thus obtained is converted to a suitable derivative (2), in which the group L acts as a better leaving group for the coupling reaction with the appropriate base to give after removal of the hydroxy protective groups the $2^1$-deoxy-$2^1,2^1$-D-ribofuranosyl difluoronucleosides of formula (II). The chemistry is summarized hereinbelow:

Even though, U.S. Pat. Nos. 4,526,988, 4,692,434 and 4,808,614 mention that any protective group to which chemists are accustomed can be employed, however, the use of silyl hydroxy-protecting groups, specially the tert-butyldimethylsilyl group are preferred since these are difficult to cleave under normal conditions and can be removed only by contact with an hydrohalic acid. The reduction of the keto function of lactone (III) to the hydroxy compound (IV) is achieved using reducing agents such as diisobutyl aluminium hydride, lithium aluminium hydride, etc.

The suitable leaving groups of compound (IV) for reaction with the base are those normally employed in organic synthesis such as methanesulfonyl, acetate, halo etc.

However, the method disclosed U.S. Pat. Nos. 4,526,988, 4,692,434 and 4,808,614 utilizes expensive hydroxy protective group like tert-butyldimethylsilyl group and reducing agents like diisobutyl aluminium hydride, lithium aluminium hydride, which, moreover, are hazardous, requiring special handling care, thereby increasing the cost and risk of manufacture.

Further, the lactone of formula (III), by virtue of having a chiral center is obtained as a mixture of erythro and threo enantiomers, of which the former one is preferred since it is the biologically more active one and provides a carbohydrate having the stereochemistry of naturally occurring ribose. More often than not, recourse to tedious and expensive chromatography procedures are taken to separate the said enantiomers.

In addition, a second chiral centre is generated when the lactone (III) is reduced to the hydroxy compound (IV), affording a mixture of α- and β-anomers, of which the latter i.e., the β-anomer being more active biologically is preferred. The method disclosed U.S. Pat. Nos. 4,526,988,4, 692,434 and 4,808,614 produces protected $2^1$-deoxy-$2^1,2^1$-difluororibose of formula (IV) as a mixture of α- and β-anomers in a ratio of 4:1, again more often than not, requiring elaborate purification techniques to remove the undesired α-anomer, further increasing the cost of manufacture of the desired β-anomers of $2^1$-deoxy-$2^1,2^1$-D-ribofuranosyl difluoronucleosides of formula (II).

ii) Chou et al. in U.S. Pat. No. 5,223,608 teach a method for obtaining the β-anomer of gemcitabine hydrochloride of formula (IIb) or the corresponding hydrobromide salt in a purity of about 80% comprising the steps of dissolving a 1:1 mixture of α- and β-anomers in water at a temperature of about 50° C. to 100° C., followed by addition of acetone to the solution and collecting the said precipitated β-anomer of 80% purity after cooling the mixture to about −10° C. to 50° C.

U.S. Pat. No. 5,223,608 also recites a method for enriching the purity of β-anomer gemcitabine hydrochloride of formula (IIb) or the corresponding hydrobromide salt to 99% comprising subjecting the material of 80% purity as

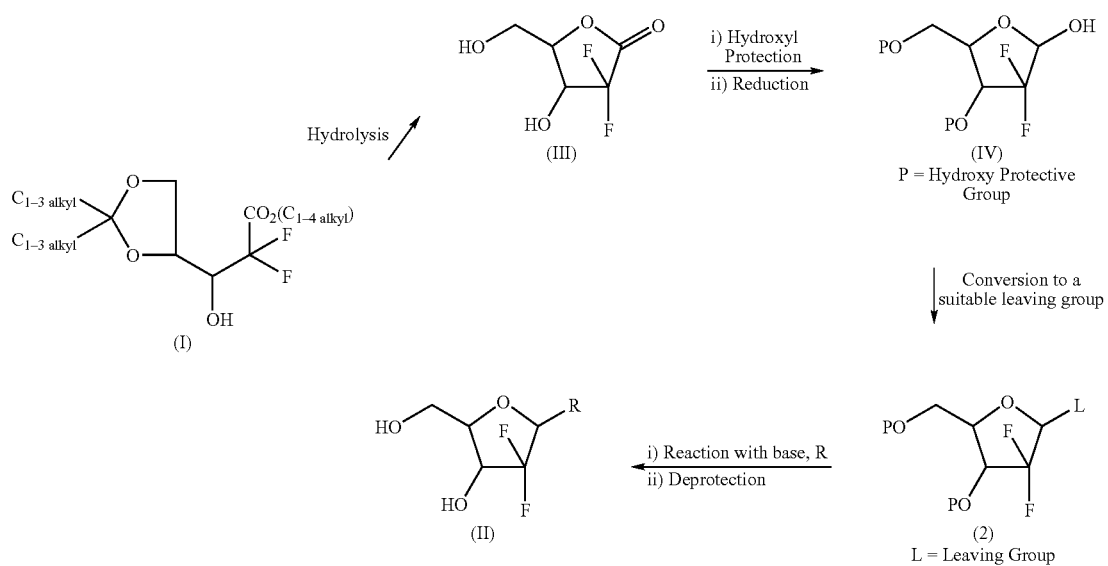

Many improvements have been reported for manufacture of $2^1$-deoxy-$2^1,2^1$-D-ribofuranosyl difluoronucleosides of formula (II) and its intermediates, which are summarized hereinbelow:

i) Chou et al. in U.S. Pat. No. 4,965,374 disclose a method for preparation of the erythro enatiomer of a lactone compound of formula (III), wherein the hydroxy protective group, P is benzoyl in greater than 95% purity comprising dissolution of a mixture of erythro and threo enantiomers in methylene chloride, cooling the solution to −5° C. to +10° C. and collecting the precipitated erythro enantiomer through filtration as such or optionally after addition of hexane.

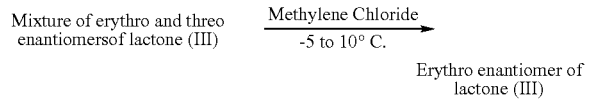

obtained by the abovementioned method to repeated purification utilizing the same purification method.

U.S. Pat. No. 5,223,608 further discloses a method for obtaining β-anomer enriched gemcitabine hydrochloride of formula (IIb) or the corresponding hydrobromide salt in a purity of 99% comprising the steps of dissolving a 1:1 mixture of α- and β-anomers in water at a temperature of about 45° C. to 90° C., followed by adjusting the pH of the solution to about 7.0 to 9.0 and collecting the said precipitated β-anomer of the free of 99% purity after cooling the mixture to about −10° C. to 30° C. The free base thus obtained is subjected to the same crystallization method in the presence of hydrogen chloride or hydrogen bromide to afford the desired gemcitabine hydrochloride of formula (IIb) or the corresponding hydrobromide salt in an anomeric purity of about 99% of the β-anomer.

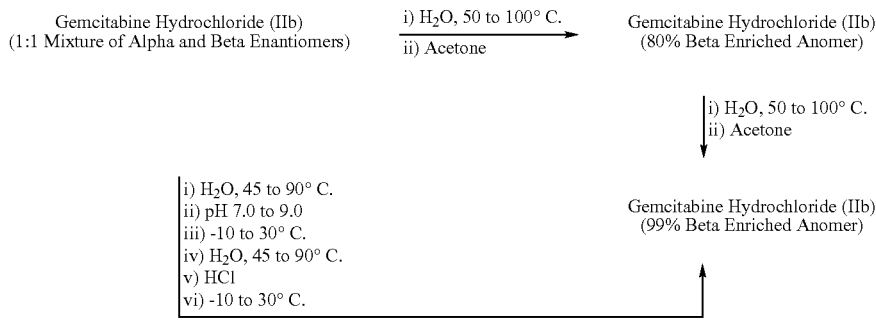

The methods disclosed in U.S. Pat. No. 5,223,608, however, suffer from a disadvantage in that repeated crystallization steps are required to obtain the product of 99% purity, not only increasing the length but also the cost of manufacture.

iii) Chou et al. in U.S. Pat. No. 5,252,756 disclose a stereoselective process for preparation of a β-enriched anomer of compound of formula (2), wherein the leaving group L is selected from an arylsulfonate or substituted arylsulfonate comprising contacting the lactol of formula (IV) with a sulfonating reagent in an inert solvent in the presence of an acid scavenger.

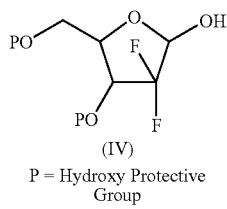

(IV)
P = Hydroxy Protective Group

Sulfonating reagent;
Inert organic solvent
Acid Scavenger

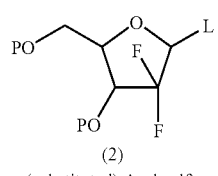

(2)
L = (substituted) Aryl sulfonate iv) Chou et al. in U.S. Pat. No. 5,256,797 further describe a method for separation of a mixture of α- and β-anomers of compound of formula (2), wherein the leaving group L is selected from an alkylsulfonate or substituted alkylsulfonate comprising contacting the anomeric mixture with a solvent, heating the mixture and adding a counter-solvent, followed by lowering the temperature to effect separation of the two enantiomers.

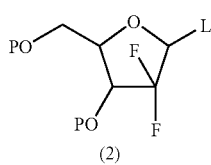

(2)
L = (substituted) Alkylsulfonate
Anomeric Mixture of Alpha and Beta Anomers i) Dissolution in Organic solvent under heating
ii) Addition of counter-solvent
iii) Cooling -continued Alpha/Beta enriched Anomer v) Chou et al. in U.S. Pat. No. 5,256,798 disclose a method for preparation of a α-anomer enriched anomer of compound (2), wherein the leaving group L is a sulfonate from the corresponding β-anomer of formula comprising treating the latter with a source of conjugate anion of a sulfonic acid at elevated temperatures in an inert solvent.

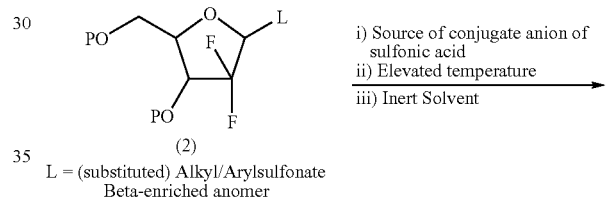

(2)
L = (substituted) Alkyl/Arylsulfonate
Beta-enriched anomer i) Source of conjugate anion of sulfonic acid
ii) Elevated temperature
iii) Inert Solvent Alpha enriched Anomer vi) Chou et al. in U.S. Pat. No. 5,371,210 and U.S. Pat. No. 5,401,838 describe a stereoselective fusion glycosylation process for preparation of β-anomer of $2^1$-deoxy-$2^1$,$2^1$-D-ribofuranosyl difluoronucleosides of formula (II), wherein R and P are as defined hereinbefore comprising reacting a difluorocarbohydrate of formula (2), wherein L is an aryl/alkyl sulfonoyloxy group as a mixture of α- and β-anomers in a ratio equal to greater than 1:1 with an excess of at least 3 molar equivalents of amino/hydroxy protected base, R at elevated temperatures of between 100° C. to 160° C., in the absence of a catalyst followed by removal of the amino/hydroxyl protective groups to give the β-anomer of $2^1$-deoxy-$2^1$,$2^1$-D-ribofuranosyl difluoronucleosides of formula (II).

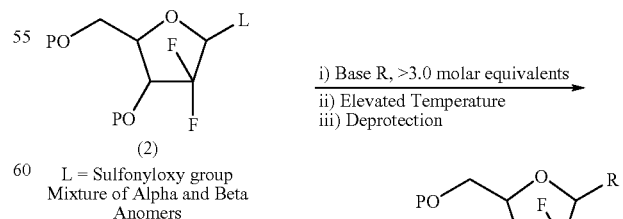

(2)
L = Sulfonyloxy group
Mixture of Alpha and Beta Anomers i) Base R, >3.0 molar equivalents
ii) Elevated Temperature
iii) Deprotection

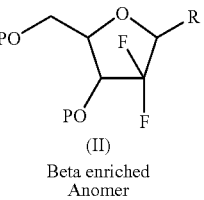

(II)
Beta enriched Anomer

The method, however, is lengthy since it involves protection and deprotection of functional groups; requires large excess of the base R and, moreover, is not highly suitable for commercial manufacture since it requires elevated temperatures for carrying out the reaction.

vii) Chou et al in U.S. Pat. No. 5,401,861 describes a method for producing an α-enriched anomer of the intermediate compound (2), wherein the leaving group is a sulfonoyloxy group comprising treating a solution of a mixture of α- and β-anomers of the the lactol compound (IV) with an amine base at very low temperature and adding a sulfonating reagent. The method, however, suffers from a limitation in that very low temperatures ranging from between −40° C. to −120° C. is employed for achieving the separation of the α- and β-anomers.

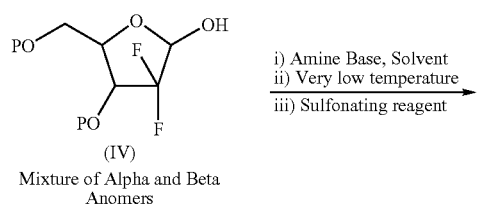

viii) Britton et al. in U.S. Pat. No. 5,420,266 disclose a process for anomerizing an α-anomer of formula (II) to the β-anomer by treatment with a hydroxide base in an organic solvent or vice versa.

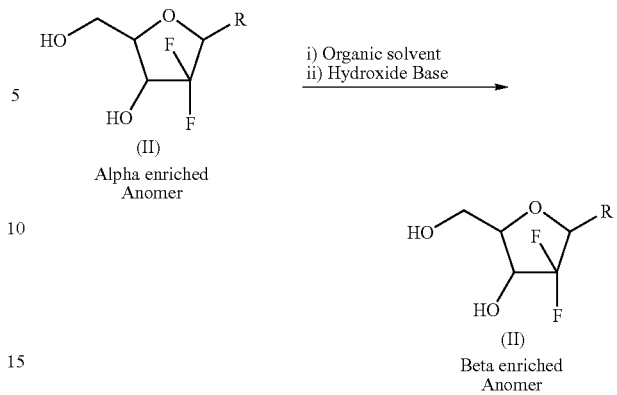

However, the product obtained contains an anomeric ratio of the α- and β-anomers in a ratio ranging between 62:38 to 97:3, which needless to mention, would require further crystallization(s) to obtain the β-anomer of at least 99% purity.

ix) Jones in U.S. Pat. No. 5,424,416 discloses a process for preparation of a β-enriched anomer of compound (II) comprising the steps of contacting a solution of the lactol of formula (IV) with a base at a temperature in the range of −40° C. to −120° C., followed by addition of a sulfonating reagent to produce an α-enriched anomer of formula (2), wherein L is a fluoroalkylsulfonoyloxy or fluoroarylsulfonoyloxy group. The compound (2) thus obtained is reacted with a conjugate anion of a sulfonic acid to give the corresponding β-enriched anomer (2), wherein L is an alkyl/arylsulfonyloxy group. The β-enriched anomer (2) thus obtained is heated to a temperature of between 50° C. to 120° C. to give the corresponding α-enriched anomer (2), wherein L is an alkyl/arylsulfonyloxy group, which on contact with a nucleobase anion, R in an inert solvent at a temperature of between 23° C. to 170° C. gives the β-enriched compound of formula (II).

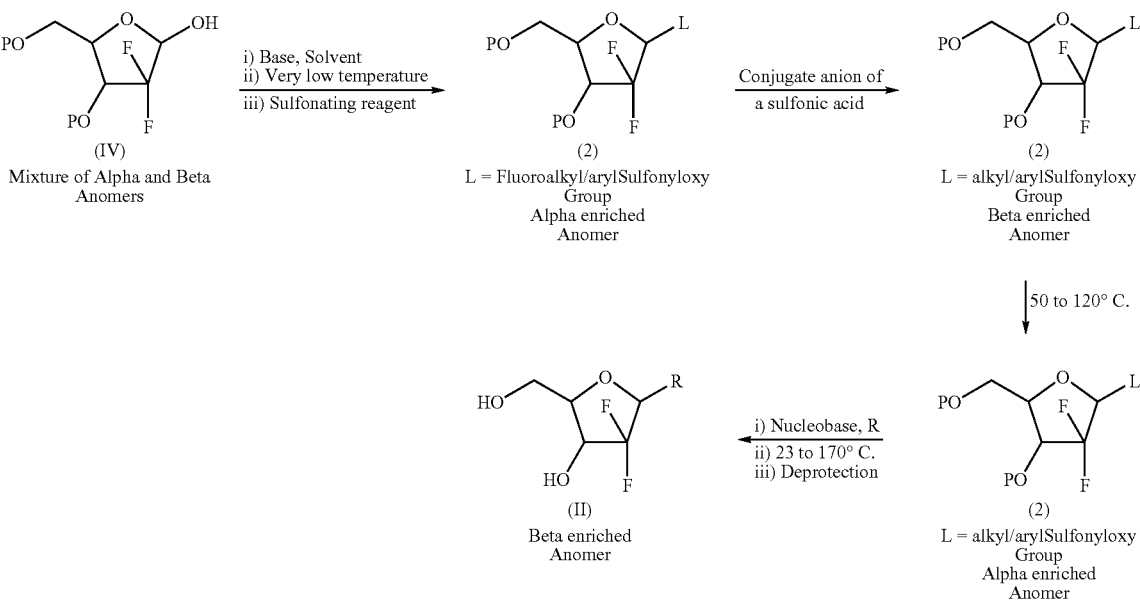

However, the length of synthesis, the very low and very elevated temperatures are major limitations of the method.

x) Kjell in U.S. Pat. No. 5,426,183 describes a catalytic stereoselective process for preparation of α- and β-enriched anomers of $2^1$-deoxy-$2^1,2^1$-D-ribofuranosyl difluoronucleosides of formula (II), wherein R and P are as defined hereinbefore comprising reacting a difluorocarbohydrate of formula (2), wherein L is a sulfonyloxy, cyano, halo, carboalkoxy groups etc. as a mixture of α- and β-anomers in a ratio equal to or greater than 1:1 with the requisite amino/hydroxy protected base, R at elevated temperatures of between 50° C. to 100° C., in the presence of a catalyst selected from potassium/barium/cesium trialkyl ammonium salts of trifluoromethanesulfonic acid, nanofluorobutanesulfonic acid, sulfuric acid, perchloric acid, nitric acid, trifluoroacetic acid etc. followed by removal of the amino/hydroxyl protective groups to give the β-anomer of $2^1$-deoxy-$2^1,2^1$-D-ribofuranosyl difluoronucleosides of formula (II).

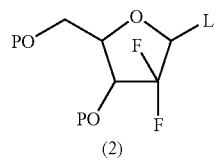

(2)
L = Sulfonyloxy group
Mixture of Alpha and Beta Anomers i) Base R,
ii) Elevated temperature
iii) Presence of a catalyst

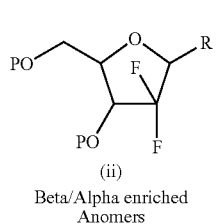

(ii)
Beta/Alpha enriched Anomers xi) Hertel et al. in U.S. Pat. No. 5,480,992 and its divisional U.S. Pat. No. 5,541,345 describe another process for preparation of $2^1$-deoxy-$2^1,2^1$-D-ribofuranosyl difluoronucleosides of formula (II), wherein R and P are as defined hereinbefore comprising reacting a amine of formula (3) with an acyclic compound of formula (4), wherein the group Y is hydrogen, alkyl or halo followed by cyclization and deprotection to give compound (II).

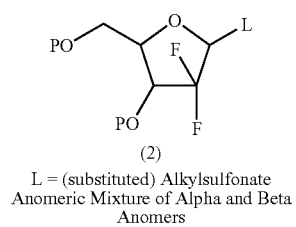

(2)
L = (substituted) Alkylsulfonate
Anomeric Mixture of Alpha and Beta Anomers i) Dissolution in Organic solvent under heating
ii) Addition of counter-solvent
iii) Cooling Alpha/Beta enriched Anomer xii) Chou et al. in U.S. Pat. No. 5,453,499 describe a stereoselective process for preparation of α-anomer of a halo compound of formula (2), wherein the group L is a halogen from the corresponding β-anomeric compounds wherein the group L is a sulfonyloxy group comprising treating the latter with a source of halide ions in an inert solvent. The halo compounds are intermediates for compound of formula (II).

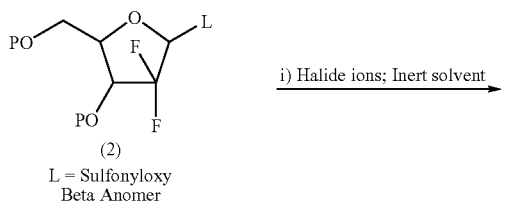

(2)
L = Sulfonyloxy
Beta Anomer i) Halide ions; Inert solvent

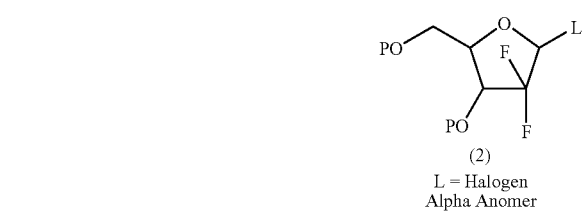

(2)
L = Halogen
Alpha Anomer xiii) Wildfeur in U.S. Pat. No. 5,521,294 describes a method for gemcitabine of formula (IIb) comprising reacting the requisite cytosine with an intermediate of formula (5).

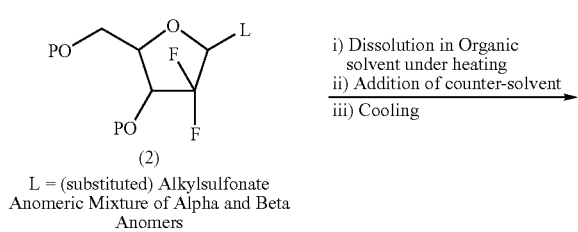

(2)
L = (substituted) Alkylsulfonate
Anomeric Mixture of Alpha and Beta Anomers i) Dissolution in Organic solvent under heating
ii) Addition of counter-solvent
iii) Cooling Alpha/Beta enriched Anomer xiv) Wirth et al. in U.S. Pat. No. 5,559,222 and its divisional, U.S. Pat. No. 5,608,043 disclose a process for preparation of gemcitabine hydrochloride of formula (IIb), which is essentially an improvement of the one described in U.S. Pat. No. 4,526,988; U.S. Pat. No. 4,692,434 and U.S. Pat. No. 4,808,614, the improvement comprising converting the lactol compound of formula (IV) to the 5-O-triphenylmethyl derivative (6), followed by reaction with methanesulfonyl chloride to give the mesyl derivative (7). The mesyl derivative (7) is then reacted with a silylated pyrimidine base, followed by removal of protective groups to give a gemcitabine derivative as a mixture of anomers, which on treatment with a base gives the β-anomer of 98% purity.

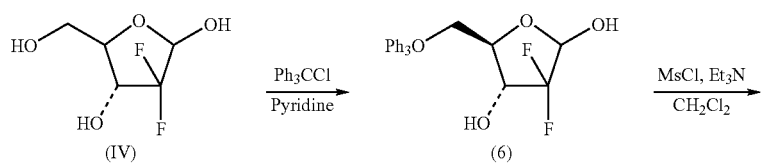
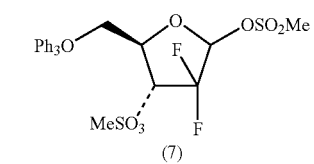
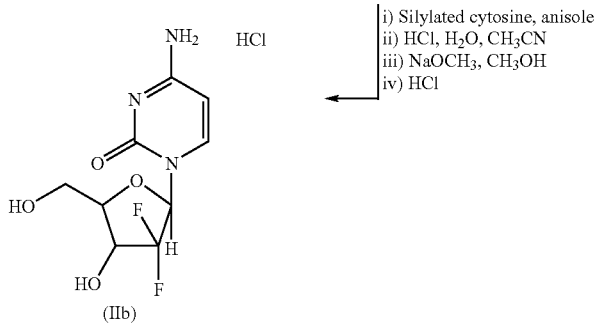

However, the overall yield reported for the process is only 1.3% from compound (IV), which renders it not at all attractive on a commercial scale.

xv) Chou in U.S. Pat. No. 5,594,124 discloses a stereoselective process for preparation of a β-enriched anomer of compound (II) comprising glycosylation of compound (2), wherein the group L is sulfonyloxy with the nucleobase, R at a temperature ranging from −120° C. to 25° C. in a low freezing inert solvent selected from dichloromethane, 1,2-dichloroethane, dichlorofluoromethane, acetone, toluene, anisole, chlorobenzene or mixture thereof. However, utilization of very low temperatures is a limitation of this process.

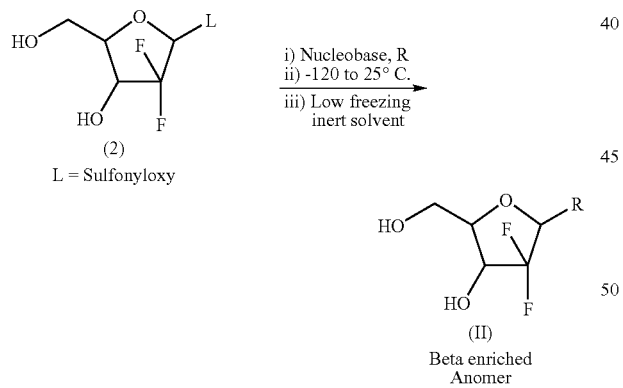

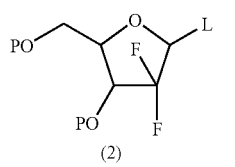

xvi) In a variation, of the above process, Chou et al. in U.S. Pat. No. 5,606,048 recite a glycosylation process wherein it is carried out in a high boiling inert solvent selected from toluene, xylenes, 1,2-dichloroethane, 1,1,2-trichloroethane, glyme, diglyme, dichlorobromoethane, dibromochloromethane, tribromomethane, dibromomethane, anisole and mixtures thereof. The method, however, is lengthy since it involves protection and deprotection of functional groups; requires large excess of the base R and moreover, is not highly suitable for commercial manufacture since it requires elevated temperatures for carrying out the reaction.

xvii) Kjell in U.S. Pat. No. 5,633,367 recites a process for preparation of compound of formula (II) comprising reacting 2-ketonucleoside of formula (8) with diethylammonium sulfur trifluoride (DAST) in the presence of catalytic amount of pyridinium hydrofluoride and a non-reactive halogenated hydrocarbon.

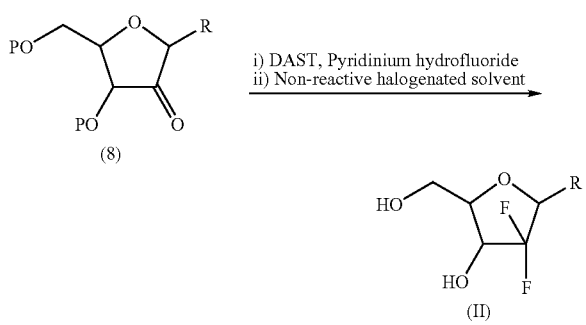

xviii) Berglund in U.S. Pat. No. 5,637,688 and its continuation U.S. Pat. No. 5,808,048 discloses a method for preparation of gemcitabine hydrochloride of formula (IIb) comprising removal of the benzoyl protective group of the β-anomer of 1-(2$^1$-deoxy-2$^1$,2$^1$-difluoro-3$^1$,5$^1$-di-O-benzoyl-D-ribofuranosyl)-4-aminopyrimidin-2-one (9) with a catalytic amount of an alkylamine in the presence of methanol or ethanol in an environment free of water, followed by treatment of the deblocked nucleoside with hydrochloric acid and an antisolvent selected from acetone, acetonitrile, tetrahydrofuran, propanol, butanol, isobutanol, sec-butanol and isopropanol and recovering gemcitabine hydrochloride (IIb) from thereof. The method has a severe limitation in that the deblocking reaction requires strictly anhydrous conditions with all reagents and solvents used free of water.

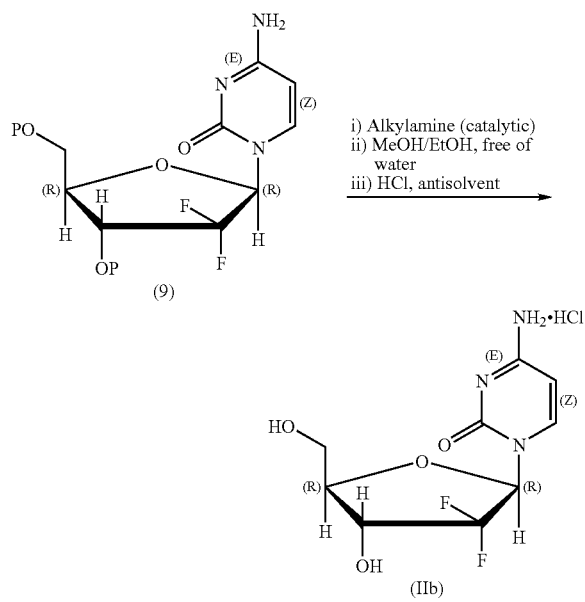

In addition, as per the disclosure of U.S. Pat. No. 4,965,374; U.S. Pat. No. 5,223,608; U.S. Pat. No. 5,434,254; and U.S. Pat. No. 5,945,547 and as described in Examples 7, 8, 9, 10, 11, 12, and 13 therein for synthesis of gemcitabine hydrochloride of formula (IIb) it would be further evident that:

a) The removal of the benzoyl protective group of the di-O-benzoyl protected gemcitabine obtained as per the method described in Examples 7 and 11 is achieved through bubbling ammonia gas through a solution of the said di-O-benzoyl protected gemcitabine in methanol, followed by evaporation of methanol and extraction of the oily residue in ethyl acetate to give gemcitabine as a 1:1 mixture of α- and β-anomers. Use of ammonia gas requires special handling and safety precautions, thereby increasing the cost and risk of manufacture.

b) The gemcitabine obtained from step (a) above is invariably obtained as an oil and is converted to the hyrochloride salt by dissolving the oil in hot isopropanol (60° C.), followed by addition of Reagent Grade hydrochloric acid and allowing the solution to cool under refrigerated conditions overnight, wherein solid gemcitabine hydrochloride as a 1:1 mixture of α- and β-anomers separates out and is collected c) The hydrochloride salt obtained in step (b) requires further purification steps as mentioned hereinbefore, viz. repeated crystallization from acetone-water mixture at 50° C. 100° C., repeated crystallization from water at a pH of 7.0 to 9.9 etc. to obtain a material of pharmaceutical grade, all the abovementioned unit operations resulting in the β-anomer of gemcitabine hydrochloride in a yield of about 0.14% to 0.33% only.

Further, it might be noted that a manufacturing process for the β-anomer of gemcitabine or its salts is invariably associated with formation of by-products, specially the corresponding α-anomer and cytosine of formula (V).

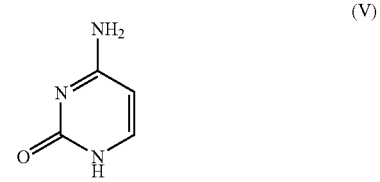

Pharmacopoeial specifications world over are very stringent on the level of the abovementioned impurities present in gemcitabine hydrochloride, which should not be more than 0.1% each.

From the foregoing it would be noticed that the prior art methods for synthesis of $2^1$-deoxy-$2^1$,$2^1$-D-ribofuranosyl difluoronucleosides of formula (II), and gemcitabine hydrochloride of formula (IIb) suffer from anyone or more of the following limitations, viz., i) utilization of expensive hydroxy protective group like tert-butyldimethylsilyl group and reducing agents like diisobutyl aluminium hydride, lithium aluminium hydride, which, moreover, are hazardous, requiring special handling care, thereby increasing the cost and risk of manufacture;

ii) utilization of multiple protection and deprotection steps not only increasing the length and cost of manufacture;

iii) utilization of high boiling solvents and elevated reaction temperatures necessitating high energy consumption;

iv) utilization of very low temperatures of about −120° C., which is not practical on a commercial scale;

v) utilization of large excess of the nucleoside base, which while adding to the cost also necessitates elaborate methods for removal of the excess reagent;

vi) utilization of gaseous ammonia and strictly anhydrous conditions for removal of certain protective groups, necessitating special handling and safety precautions;

vii) more often than not, resulting in formation of predominant amounts of the undesired α-anomers;

viii) utilization of expensive and tedious chromatographic procedures and multiple crystallization techniques for obtaining the therapeutically desirable β-enriched anomers, not only increasing the length and cost of manufacture; and ix) production of the object $2^1$-deoxy-$2^1$,$2^1$-D-ribofuranosyl difluoronucleosides of formula (II), and gemcitabine hydrochloride of formula (IIb) in rather poor yields.

A need, therefore, exists for an improved method for manufacture of $2^1$-deoxy-$2^1$,$2^1$-D-ribofuranosyl difluoronucleosides of formula (II), in particular gemcitabine hydrochloride of formula (IIb), which is free of and not associated with the limitations of the prior art and provides the object compounds in higher yields and conforming to pharmacopoeial specifications.

OBJECTS OF THE INVENTION

An object of the present invention is to provide a process for preparation of $2^1$-deoxy-$2^1$,$2^1$-D-ribofuranosyl difluoronucleosides of formula (II), in particular gemcitabine hydrochloride of formula (IIb), which is free of the limitations of the prior art methods.

Another object of the present invention is to provide a novel intermediate for preparation of $2^1$-deoxy-$2^1$-D- ribofuranosyl difluoronucleosides of formula (II), in particular gemcitabine hydrochloride of formula (IIb).

Yet another object of the present invention is to provide a process for preparation of the novel intermediate for $2^1$-deoxy-$2^1$,$2^1$-D-ribofuranosyl difluoronucleosides of formula (II), in particular gemcitabine hydrochloride of formula (IIb).

A further object of the present invention is to provide a process for preparation of the β-enriched anomer of $2^1$-deoxy-$2^1$,$2^1$-D-ribofuranosyl difluoronucleosides of formula (II), in particular gemcitabine hydrochloride of formula (IIb), which is simple, cost-effective and avoids use of hazardous and expensive reagents and solvents and moreover, does not require strictly anhydrous conditions and special handling and safety precautions.

Yet further object of the present invention is to provide a process for preparation of $2^1$-deoxy-$2^1$,$2^1$-D-ribofuranosyl difluoronucleosides of formula (II), in particular gemcitabine hydrochloride of formula (IIb) in higher yields.

Another object of the present invention is to provide a process for preparation of $2^1$-deoxy-$2^1$,$2^1$-D-ribofuranosyl difluoronucleosides of formula (II), in particular gemcitabine hydrochloride of formula (IIb), which utilizes a simple and less laborious purification method.

Yet, another object of the present invention is to provide a process for preparation of $2^1$-deoxy-$2^1$,$2^1$-D-ribofuranosyl difluoronucleosides of formula (II), in particular gemcitabine hydrochloride of formula (IIb) conforming to pharmacopoeial specifications.

SUMMARY OF THE INVENTION

In their endeavour to provide an improved process for manufacture of $2^1$-deoxy-$2^1$,$2^1$-D-ribofuranosyl difluoronucleosides of formula (II), in particular gemcitabine hydrochloride of formula (IIb), the present inventors found that most, if not all of the limitations of the prior art could be addressed through utilization of:
a) a novel intermediate for synthesis of the object compounds;
b) less expensive, less hazardous reagents and solvents; and
c) a novel and simple crystallization method, These aspects which form the basis of the present invention and are discussed in detail hereinbelow:

In the first place, the present inventors have found the hydroxy function of the lactol compound of formula (IV) could be reacted with trichloroacetonitrile in the presence of a base to give the corresponding trichloroacetimidate of formula (I),

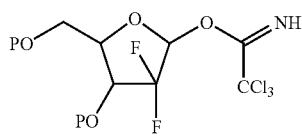

(I)

which is novel and not reported hitherto before.

The preparation of the trichloroacetimidate of formula (I) the other reactive derivatives utilized in the prior art and discussed in detail hereinbefore is simple in that it does not require any special or elaborate precautions, economical in that it does away with utilization of expensive reagents and moreover, the product is obtained in near quantitative yield.

Secondly, it was found that the trichloroacetimidate of formula (I) undergoes the glycosyslation reaction with the nucleobase, R in a highly stereoselective manner to provide the β-enriched anomer of $2^1$-deoxy-$2^1$,$2^1$-D-ribofuranosyl difluoronucleosides of formula (II),

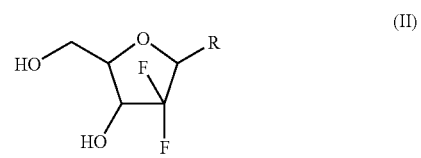

(II)

The glycosylation reaction of the nucleobase, R with the trichloroacetimidate of formula (I) is simply achieved by heating the two together in a suitable solvent, which unlike most of the prior art methods does not require elevated or very low temperatures.

Further the method does away with utilization of very large molar excess of the nucleobase and in fact a quantitative conversion could be achieved using less than or equal to 2 molar equivalents of the said nucleobase, R. This results in formation of a product in higher purity, containing less amounts of the unreacted nucelobase, which makes it more amenable to further purification in giving a product of not only very high chemical and anomeric purity, thereby rendering the method vastly superior over the prior art methods.

Further, it was found the removal of the protective groups of the product obtained after the aforesaid glycosylation reaction, unlike the prior art methods does not require strict anhydrous conditions and could be simply achieved by contacting the protected difluoronucleoside with aqueous ammonia in an alcoholic solvent, from which the deprotected product (II) could be isolated as predominantly the β-anomer. Alternatively, the deprotection can also be achieved by contacting the protected compound with hydroxy ion exchanged anion exchange resins.

Furthermore, it was found the pharmaceutically acceptable salts of the difluoronucleoside (II) could be prepared from the same alcoholic solvent in the which the removal of protective groups is carried by mixing the deprotected difluoronucleoside with the requisite pharmaceutically acceptable acid and a predominantly β-anomer of the salt could be isolated in high chemical and anomeric purity of ≧95% and more often than not ≧99%, complying with pharmacopoeial specifications in just one crystallization step.

In addition, it was found that both the chemical and anomeric purity could be further enhanced by optional purification of the difluoronucleoside (II) from a mixture of an aliphatic acid and water, which is again novel and hitherto not reported.

Last, but not the least it was also found that the lactol compound could be obtained from the corresponding lactone compound (III) by reducing the latter with sodium bis(2-methoxyethoxy)aluminium hydride, commonly known as Vitride, which unlike the other hydride reducing agents utilized in the prior art is less pyrophoric, does not require very low cryogenic temperatures and in fact and can be carried out at temperatures in the range of between −20° C. to −30° C.

Thus in accordance with the foregoing, In one aspect the present invention provides a novel intermediate of formula (I),

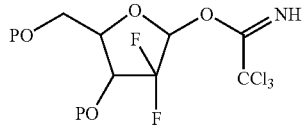

wherein P is hydrogen or a hydroxy protective group, useful for preparation of $2^1$-deoxy-$2^1,2^1$-D-ribofuranosyl difluoronucleosides of formula (II), wherein R is a

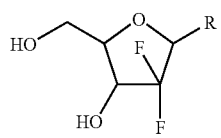

nucleobase selected from a purine or pyrimidine

In another aspect the present invention provides a novel intermediate of formula (I)

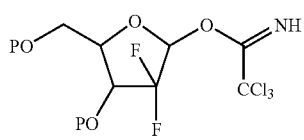

useful for preparation of gemcitabine hydrochloride of formula (IIb).

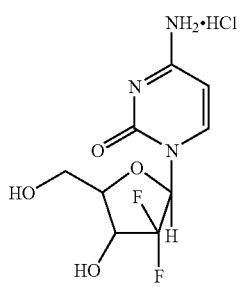

In yet another aspect, the present invention provides a process for preparation of the novel intermediate of formula (I) comprising reaction of the lactol compound of formula (IV), wherein P is as defined hereinbefore with trichloroacetonitrile in an inert organic solvent and in the presence of a base.

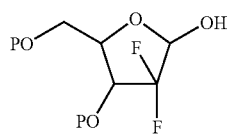

In a further aspect the present invention provides a simple, convenient and cost effective process for preparation of the novel intermediate of formula (I) comprising reduction of the lactone compound of formula (III),

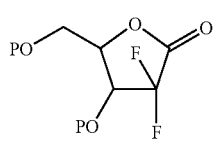

wherein P is as defined hereinbefore with sodium bis(2-methoxyethoxy)aluminium hydride, commonly known as vitride in an inert organic solvent at a temperature of between –20° C. to –30° C. to give the lactol compound of formula (IV) and reacting the compound of formula (IV) thus obtained with trichloroacetonitrile in an inert organic solvent and in the presence of a base to give the intermediate of formula (I).

In yet further aspect the present invention provides a process for preparation of $2^1$-deoxy-$2^1,2^1$-D-ribofuranosyl difluoronucleosides of formula (II),

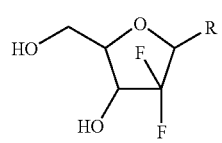

wherein R is a nucleobase selected from a purine or pyrimidine comprising glycosylation of the novel intermediate of formula (I),

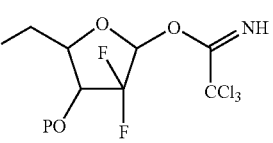

wherein P is as defined hereinbefore with a purine or pyrimidine base R, wherein R is selected from

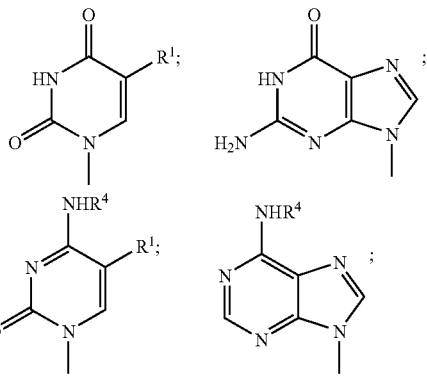

-continued

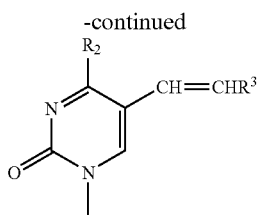

and wherein R¹ is hydrogen, alkyl, or halogen; R² is hydroxy; R³ is hydrogen or halogen; and R⁴ is hydrogen or a nitrogen protective group in the presence of an inert organic solvent and optionally in the presence of a Lewis acid catalyst, followed by removal of the protective groups to give compound of formula (II).

In another aspect the present invention provides a process for preparation of gemcitabine hydrochloride of formula (IIb),

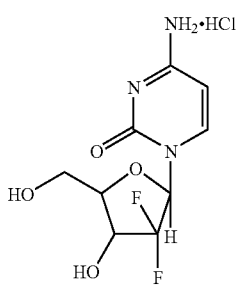
(IIb)

comprising glycosylation of the novel intermediate of formula (I)

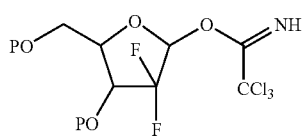
(I)

with cytosine of formula (Va) or (Vb),

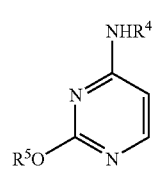
(Va)

(Vb)

wherein R⁴ is a nitrogen protective group and R⁵ is a hydroxy protective group in the presence of an inert organic solvent and optionally in the presence of a Lewis acid catalyst, followed by removal of the protective groups and contacting the gemcitabine free base thus obtained with hydrogen chloride to give gemcitabine hydrochloride of formula (IIb).

In yet another aspect the present invention provides a stereoselective glycosylation process for preparation of the β-enriched anomer of 2¹-deoxy-2¹,2¹-D-ribofuranosyl difluoronucleosides of formula (II),

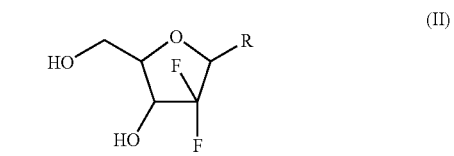
(II)

wherein R is a nucleobase selected from a purine or pyrimidine comprising the steps of
a) glycosylation of the novel intermediate of formula (I),

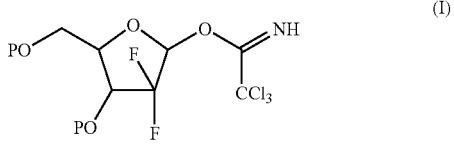
(I)

wherein P is as defined hereinbefore with a purine or pyrimidine base R, wherein R is selected from

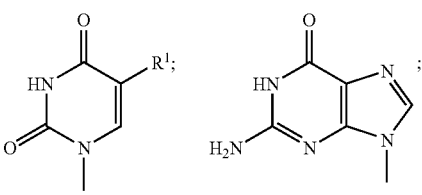

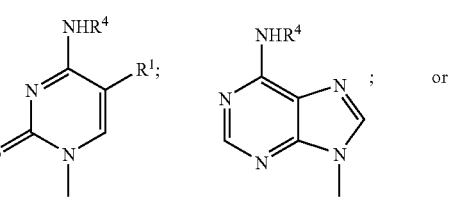
; or

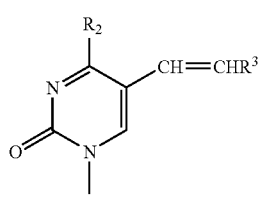

wherein $R^1$ is hydrogen, alkyl, or halogen; $R^2$ is hydroxy; $R^3$ is hydrogen or halogen; and $R^4$ is hydrogen or a nitrogen protective group in the presence of an inert organic solvent and optionally in the presence of a Lewis acid catalyst to give a protected $2^1$-deoxy-$2^1,2^1$-D-ribofuranosyl difluoronucleosides of formula (IIA),

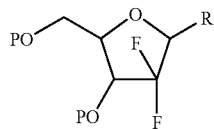

(IIA)

wherein P is as defined as hereinbefore;

b) removal of the protective groups by treatment of compound of formula (IIA) with aqueous ammonia in the presence of a $C_{1-3}$ alcohol or with hydroxy ion exchanged anion exchange resins to give the β-enriched anomer of the free base of compound of formula (II);

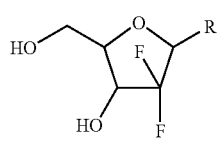

(II)

c) contacting the free base of compound of formula (II) thus obtained with a pharmaceutically acceptable acid in a $C_{1-3}$ alcohol to give the corresponding the β-enriched anomer of its pharmaceutically acceptable acid addition thereof; and d) optionally, enriching the β-anomer content of compound of formula (II) through crystallization from a mixture of a $C_{2-3}$ aliphatic organic acid and water.

In a further aspect the present invention provides a stereoselective glycosylation process for preparation of greater than 99% β-enriched anomer of gemcitabine hydrochloride formula (IIb)

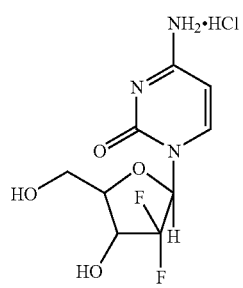

(IIb)

comprising the steps of a) glycosylation of the novel intermediate of formula (I),

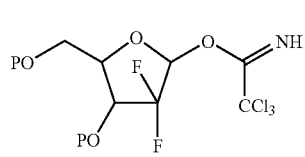

(I)

wherein P is as defined hereinbefore with cytosine of formula (Va) or (Vb),

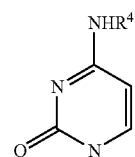

(Va)

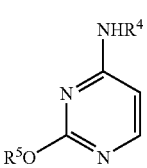

(Vb)

wherein $R^4$ is a nitrogen protective group and $R^5$ is a hydroxy protective group in the presence of an inert organic solvent and optionally in the presence of a Lewis acid catalyst to protected gemcitabine free base of formula (IIa), wherein P and $R^4$ are as defined hereinbefore;

b) removal of the protective groups by treatment of compound of formula (IIa) with aqueous ammonia in the presence of a $C_{1-3}$ alcohol a or with hydroxy ion exchanged anion exchange resins to give the β-enriched anomer of gemcitabine free base of formula (IIc);

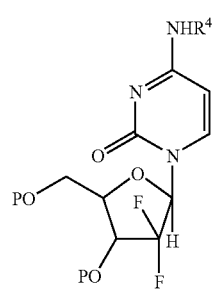

(IIa)

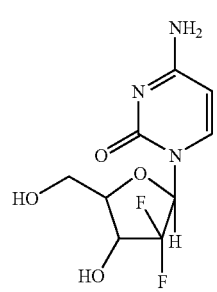

(IIc)

c) contacting the gemcitabine free base of formula (IIc) thus obtained with hydrogen chloride in a $C_{1-3}$ alcohol to give the β-enriched anomer of gemcitabine hydrochloride of formula (IIb) in ≧95%, preferably ≧99% purity; and d) optionally further enriching the β-anomer content of gemcitabine hydrochloride of formula (IIb) to greater than 99% through crystallization from a mixture of a $C_{2-3}$ aliphatic organic acid and water.

DETAILED DESCRIPTION OF THE INVENTION

Preparation of the Novel Intermediate of Formula (I)

The trichloroacetimidate compound of formula (I) can be prepared by reacting the lactol compound of formula (IV) with trichloroacetonitrile in an inert organic solvent and in the presence of a base.

The hydroxy protecting group, P in both compounds of formula (IV) and (I) are ones that are routinely utilized in organic synthesis and may represent, but however, not limited to formyl, 2-chloroacetyl, benzyl, diphenylmethyl, triphenyl methyl, 4-nitrobenzyl, phenoxycarbonyl, tertiary butyl, methoxymethyl, tetyrahydropyranyl, allyl, tetrahydrothienyl, 2-methoxethoxy methyl, methoxy acetyl, phenoxy acetyl, isobutyryl, ethoxy carbonyl, benzyloxy carbonyl, mesyl, trimethylsilyl, isopropyl dimethylsilyl, methyldiisopropyl silyl, triisopropyl silyl, tertiary butyldimethyl silyl etc.

Suitable inert organic solvents that can be employed are those which are water-immiscible, which apart from their non-participation in the essential reaction are able to form a two-phase system with water. Such a solvent offers advantage in not only effecting an efficient conversion but also helps in isolation of the product by simple evaporation of the solvent or through work up by addition of water.

Suitable inert water-immiscible organic solvents that can be employed include halogenated e.g. chlorinated hydrocarbons, e.g. dichloromethane and 1,2-dichloroethane; esters e.g. acetic acid $(C_{1-4})$ alkyl esters e.g. ethyl acetate; ethers e.g. diisopropylether; aromatic hydrocarbons eg. toluene, xylenes etc. Chlorinated hydrocarbons are preferred and amongst these dichloromethane and 1,2-dichloroethane are the most preferred.

While both organic and inorganic bases can be utilized, however organic bases are preferred. Suitable organic bases that can be employed include but are not limited to diethylamine, triethylamine, diisopropylethyllamine, cyclohexylamine, pyridine, 2,4-dimethylamino pyridine, N-methyl morpholine etc. Triethylamine and diisopropylamine, because of their low cost are preferred.

The base can be employed in catalytic or molar proportions to the lactol compound of formula (IV) or in excess thereof. Preferably it is employed in catalytic amounts.

Trichloroacetonitrile can be employed in equimolar proportions to the lactol compound of formula (IV) or in excess thereof. Usually it is employed in molar proportions of 1 to 20 moles per mole of compound of formula (IV). Preferably, the base is employed in molar proportions of 1-1.5 moles per mole of compound of formula (IV).

The trichloroacetimidate formation can be generally carried out by addition of the lactol compound (IV) to a mixture of trichloroacetonitrile and the base in the inert organic solvent at a temperature ranging between −20° C. to 20° C. and thereafter agitating the reaction mixture at ambient temperature in the range of between 20° C. to 30° C. for a period of 3 to 10 hours till completion of reaction.

The trichloroacetimidate (I) thus formed can be isolated by simple evaporation of the solvent or it can be isolated by addition of water to the reaction mixture, separation of the organic phase from the aqueous phase, followed by evaporation of the organic solvent and the product thus obtained can be used for the next step of glycosylation reaction with the nucleobase, R as such without any purification.

Alternatively, the reaction mixture after completion of reaction can be washed with water, the separated organic phase can be dried over suitable dehydrating agents and the solution as such without isolation can be used for next step of glycosylation reaction with the nucleobase, R The compound of formula (I) normally obtained as an oil can be either the α-anomer or the β-anomer or mixtures thereof.

A typical compound of formula (I), wherein the protective group, P is benzoyl and represented by compound of formula (Ia) obtained by the abovementioned method was found to possesses the following spectral and physical characteristics, viz.

$^1$H NMR (CDCl$_3$, δ): 8.7 (s, NH, 1H), 7.36-8.1 (m, Ar, 10H), 6.51-6.59 (dd, H-1, 1H), 5.59-5.66 (dd, H-3 1H), 4.64-4.83 (m, H-5 2H, H-4 1H) $^{13}$C NMR (CDCl$_3$, δ): 164.7-165.9 (C=NH), 127.9-130 (Ar), 121.3 (C-2), 97.58 (C-1), 90 (CCl3), 78.8 (C-4), 71.9 (C-3), 63.8 (C-5). Mass Spectrum (M$^+$): 522.3 Specific rotation +15 to +60°

The lactol compound (IV) in turn can be prepared from the lactone compound (III) through reduction with sodium bis(2-methoxyethoxy)aluminium hydride, commonly known as vitride in an inert organic solvent at a temperature of between −20° C. to −30° C.

Vitride (CAS Reg. No. [22722-98-1]) is available commercially as a 70% solution in toluene, which can be used as such for reducing the lactone (III). Unlike other hydride reducing agents such as lithium aluminium hydride, lithium tertiarybutoxy aluminium hydride, diisobutyl lithium aluminium hydride etc. vitride is comparatively a reducing agent of moderate strength, less pyrophoric, oxygen stablepumpable liquid, not requiring very low cryogenic temperatures and compatible with most of the ubiquitous aprotic solvents, thereby offering many advantages in its utilization in the process.

Typically, the reduction can be carried out by reacting the commercially available 70% solution of vitride in toluene with a solution of the lactone compound (III) in a suitable aprotic solvent under an inert gas atmosphere at a temperature of between −20° C. to −30° C. for a period of 1 to 2 hrs. The lactol compound (IV) could be isolated by routine work-up procedures.

Suitable aprotic solvents that can be employed include tetrahydrofuran, dioxane, N,N-dimethylformamide, N,N-dimethylacetamide etc.

Typically, the product can be isolated by quenching the reaction mixture with 6N hydrochloric acid, followed by extraction with a water-immiscible organic solvent. Evaporation of the organic solvent afford the lactol (IV).

The vitride can be employed in equimolar proportions to the lactone compound of formula (III) or in excess thereof. Usually it is employed in molar proportions of 1 to 3 moles per mole of compound of formula (III). Preferably it is employed in molar proportions of 1-1.5 moles per mole of compound of formula (III).

Preparation of $2^1$-deoxy-$2^1$,$2^1$-D-ribofuranosyl difluoronucleosides of formula (II)

The $2^1$-deoxy-$2^1$,$2^1$-D-ribofuranosyl difluoronucleosides of formula (II) can be prepared by glycosylation of the intermediate compound of formula (I), wherein the protective group, P is as defined hereinbefore with the requisite nucleobase, R The nucleobase R can be selected from anyone of a pyrimidine or a purine compound represented by the structures shown in Chart-I.

In compounds represented in Chart-I, $R^1$ can be hydrogen, alkyl, or halogen; while is $R^2$ is hydroxy; and whereas $R^3$ is hydrogen or halogen; $R^4$ can be hydrogen or a nitrogen protective group. Alkyl is typically a lower alkyl of 1 to 4 carbon atoms, while halogen represents chlorine, bromine, iodine or fluorine; whereas the nitrogen protective group $R^4$ are those that are routinely utilized in organic synthesis, in particular acetyl and trialkylsilyl protective groups being preferred.

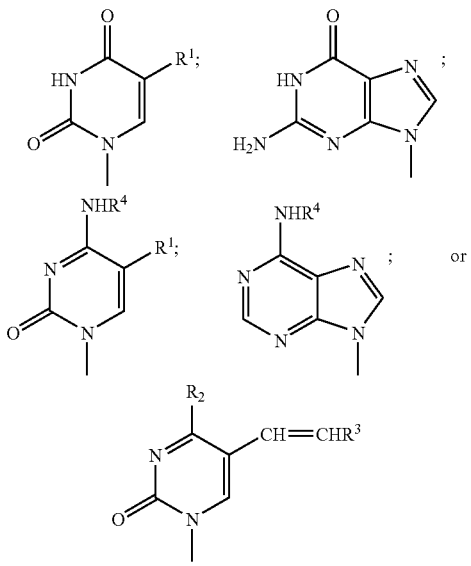

The glycosylation reaction is carried out by reaction of compound of formula (I) with anyone of the nucleobase represented in Chart-I in the presence of an inert organic solvent and optionally in the presence of a Lewis acid catalyst to give a protected $2^1$-deoxy-$2^1,2^1$-D-ribofuranosyl difluoronucleosides of formula (IIA), wherein P and R are as defined hereinbefore.

Suitable inert organic solvents that can be employed include but are not limited to acetonitrile, toluene, xylene and its isomers, chlorobenzene, ortho-dichlorobenzene, dichloromethane, 1,1-dichloroethane, 1,2-dichloroethane, 1,1,2-trichloroethane, anisol. The preferred inert solvent is 1,2-dichloroethane.

Suitable Lewis acid catalysts that can be employed are selected as tin tetrachloride, trimethylsilyltrifluoromethanesulphonate, trimethylsilyl nonafluorobutylsulphonate, trimethylsilyl perchlorate, borontrifluoride diethyletherate, trimethylsilyl tetrafluoroborate etc., preferably trimethylsilyl trifluoromethane sulphonate.

Typically, the glycosylation reaction is carried out be refluxing together compound (I), the nucleobase, R and optionally the Lewis acid catalyst in anyone of the inert organic solvent mentioned hereinbefore, till completion of reaction to give the protected $2^1$-deoxy-$2^1,2^1$-D-ribofuranosyl difluoronucleosides of formula (IIA).

The nucleobase, R can be employed in equimolar proportions to the compound of formula (I) or in excess thereof, but however, below 2 moles per mole of compound of formula (I). Usually it is employed in molar proportions of 1 to 2.0 moles per mole of compound of formula (I).

Preferably, the base is employed in molar proportions of 1-1.6 moles per mole of compound of formula (I).

The protected $2^1$-deoxy-$2^1,2^1$-D-ribofuranosyl difluoronucleosides of formula (IIA) can be isolated from the reaction mixture by conventional methods eg., addition of water to the reaction mixture and extraction of the product into a organic solvent, If the inert organic solvent utilized in the glycolsylation reaction is water-immiscible the product gets extracted automatically into the said solvent. If however, the inert organic solvent utilized in the glycolsylation reaction is a water-miscible one, then the product is extracted into any water-immiscible organic solvent such as alkyl esters eg., ethyl acetate; chlorinated hydrocarbons eg., dichloromethane. The protected compound (IIA) can be isolated by evaporation of the organic solvent.

The step of deprotection of the protective groups, P and $R^4$, if any is carried out by contacting the protected $2^1$-deoxy-$2^1,2^1$-D-ribofuranosyl difluoronucleosides of formula (IIA) with aqueous ammonia in a solvent selected from a $C_{1-3}$ alcohol or hydroxy ion exchanged anion exchange resins to give the β-enriched anomer of the free base of compound of formula (II).

The deprotection is typically carried out by agitating a solution of the protected $2^1$-deoxy-$2^1,2^1$-D-ribofuranosyl difluoronucleosides of formula (IIA) in a $C_{1-3}$ alcohol with aqueous ammonia at a temperature of between ambient to a temperature of about 60° C. for a time sufficient to effect complete removal of the protective groups to give the free base of compound of formula (II).

While, a $C_{1-3}$ alcohol selected from methanol, ethanol, 1-propanol and 2-propanol can be used, however, methanol is most preferred since the protected compounds (IIA) are generally more soluble in it than ethanol, 1-propanol and 2-propanol, by virtue of which the deprotection in methanol can be carried out at ambient temperatures of between 25° C. to 30° C., unlike the other two, more often than requiring heating or refluxing. Further, methanol offers advantage in that the salt formation of the free base could be carried out in the same solvent as well as can be crystallized from the same to afford the β-enriched anomer.

Alternatively, the deprotection can be carried out by contacting the protected compound (IIA) with an hydroxy ion exchanged anion exchange resin.

Anion exchange resins consisting of chloride as an anion are converted to the corresponding hydroxyl exchanged ones by mixing of the former with aqueous sodium hydroxide for a period of 2 to 3 hrs. The suspension is filtered, the resin bed washed successively with demineralised water till pH of the filtrate was in the range of between 6.0 to 7.0. The washed resin is further washed with a $C_{1-3}$ alcohol to effect the hydroxyl ion exchange.

The hydroxy ion exchanged resin is mixed with compound (IIA) in a $C_{1-3}$ alcohol at a temperature of from 30° C. to 50° C., preferably at a temperature of from 40° C. to 45° C. for a period of 20 to 40 hours to effect the deprotection. At the end the resin is filtered and the filtrate concentrated to give the free base of compound (II).

Suitable anion exchange resins that can be employed are strong base anion exchangers, wherein the ionic form is generally a chloride ion. Typical of such anion exchange resins are the commercially available Amberlite resins like FPA40 Cl, FPA90 Cl, FPA91 Cl, FPA97 Cl, FPA98 Cl, IRA 400, IRA402 Cl, IRA410 Cl etc.

Thus, in a typical embodiment, to a solution of the protected compound (IIA) in methanol is added a 25% aqueous solution of ammonia in water and mixture agitated at room temperature for a period of 4 to 8 hrs till completion of the deprotection. Removal of methanol by evaporation gives the free base of compound (II).

In another typical embodiment, an anion exchange resin, for instance, Amberlite IRA 400 is agitated with 5% aqueous sodium hydroxide at room temperature for 2 to 3 hrs and the resin filtered off. The filtered resin is washed successively with demineralised water till pH of the filtrate is in the range of 6.0 to 7.0. The resin is finally washed with a $C_{1-3}$ alcohol, for instance methanol. The hydroxy ion exchanged resin thus obtained is stirred with the protected compound (IIA) in methanol at a temperature of between 40° C. to 45° C. for 36 hours. At the end, the resin is filtered off and the filtrate concentrated to give the deprotected free base compound (II).

The deprotected compound (II) obtained by any of the abovementioned two methods is generally obtained as an oil and can be used as such without any purification for formation of its pharmaceutically acceptable salt.

The salt formation can be effected by contacting a solution of the free base (II) in a $C_{1-3}$ alcohol selected from methanol, ethanol, 1-propanol and 2-propanol with the requisite acid for sufficient time. The salt thus formed can be isolated or crystallized from the same alcoholic solvent or with anyone of methanol, ethanol, 1-propanol or 2-propanol to give the corresponding acid addition salt (II), generally as the β-enriched anomer.

Typical acid addition salts of compound of formula (II) that can be prepared include those salts obtained using acids such as tartaric, citric, acetic, hydrochloric, hydrobromic, sulphuric, phosphoric etc.

The anomeric and chemical purity of the acid addition salt can be enriched further, if necessary through one more crystallization of the same from with anyone of methanol, ethanol, 1-propanol or 2-propanol or optionally through crystallization from a mixture of water and a $C_{2-3}$ aliphatic organic acid, selected from acetic acid and propionic acid.

Preparation of Gemcitabine Hydrochloride of Formula (IIa)

Gemcitabine hydrochloride of formula (IIa) can be prepared by glycosylation of the intermediate compound of formula (I), wherein the protective group, P is as defined hereinbefore with the cytosine compounds of formula (Va) or (Vb), wherein $R^4$ is a nitrogen protective group and $R^5$ is a hydroxy protective group in the presence of an inert organic solvent and optionally in the presence of a Lewis acid catalyst to protected gemcitabine free base of formula (IIa).

Suitable inert organic solvents that can be employed include but are not limited to acetonitrile, toluene, xylene and its isomers, chlorobenzene, ortho-dichlorobenzene, dichloromethane, 1,1-dichloroethane, 1,2-dichloroethane, 1,1,2-trichloroethane, anisole. The preferred inert solvent is 1,2-dichloroethane.

Suitable Lewis acid catalysts that can be employed are selected as tin tetrachloride, trimethylsilyltrifluoromethanesulphonate, trimethylsilyl nonafluorobutylsulphonate, trimethylsilyl perchlorate, borontrifluoride diethyletherate, trimethylsilyl tetrafluoroborate etc., preferably trimethylsilyl trifluoromethane sulphonate.

Typically, the glycosylation reaction is carried out be refluxing together compound (I), the cytosine compounds, (Va) or (Vb) and optionally the Lewis acid catalyst in anyone of the inert organic solvent mentioned hereinbefore, till completion of reaction to give the protected gemcitabine compound of formula (IIa).

The cytosine compounds (Va) and (Vb) can be employed in equimolar proportions to the compound of formula (I) or in excess thereof, but, however, below 2 moles per mole of compound of formula (I). Usually it is employed in molar proportions of 1 to 2.0 moles per mole of compound of formula (I). Preferably, the base is employed in molar proportions of 1-1.6 moles per mole of compound of formula (I).

The protected gemcitabine of formula (IIa) can be isolated from the reaction mixture by conventional methods eg., addition of water to the reaction mixture and extraction of the product into a organic solvent, If the inert organic solvent utilized in the glycolsylation reaction is water-immiscible the product gets extracted automatically into the said solvent. If however, the inert organic solvent utilized in the glycolsylation reaction is a water-miscible one, then the product is extracted into any water-immiscible organic solvent such as alkyl esters eg., ethyl acetate; chlorinated hydrocarbons eg., dichloromethane. The protected compound (IIa) can be isolated by evaporation of the organic solvent.

The step of deprotection of the protective groups, P and $R^4$, is carried out by contacting the protected $2^1$-deoxy-$2^1$,$2^1$-D-ribofuranosyl difluoronucleosides of formula (IIa) with aqueous ammonia in a solvent selected from a $C_{1-3}$ alcohol or hydroxy ion exchanged anion exchange resins to give the β-enriched anomer of the gemcitabine free base of compound of formula (IIc).

The deprotection is typically carried out by agitating a solution of the protected $2^1$-deoxy-$2^1$,$2^1$-D-ribofuranosyl difluoronucleosides of formula (IIa) in a $C_{1-3}$ alcohol with aqueous ammonia at a temperature of between ambient to a temperature of about 60° C. for a time sufficient to effect complete removal of the protective groups to give the free base of compound of formula (II).

While a $C_{1-3}$ alcohol selected from methanol, ethanol, 1-propanol and 2-propanol can be used, however, methanol is most preferred since the protected compounds (IIA) are generally more soluble in it than ethanol, 1-propanol and 2-propanol, by virtue of which the deprotection in methanol can be carried out at ambient temperatures of between 25° C. to 30° C., unlike the other two, more often than requiring heating or refluxing. Further, methanol offers advantage in that the salt formation of the free base could be carried out in the same solvent as well as can be crystallized from the same to afford the β-enriched anomer, having purity >95%.

Alternatively, the deprotection can be carried out by contacting the protected compound (IIA) with an hydroxy ion exchanged anion exchange resin.

Anion exchange resins consisting of chloride as an anion are converted to the corresponding hydroxyl exchanged ones by mixing of the former with aqueous sodium hydroxide for a period of 2 to 3 hrs. The suspension is filtered, the resin bed washed successively with demineralised water till pH of the filtrate was in the range of between 6.0 to 7.0. The washed resin is further washed with a $C_{1-3}$ alcohol to effect the hydroxyl ion exchange.

The hydroxy ion exchanged resin is mixed with compound (IIa) in a $C_{1-3}$ alcohol at a temperature of from 30° C. to 50° C., preferably at a temperature of from 40° C. to 45° C. for a period of 20 to 40 hours to effect the deprotection. At the end the resin is filtered and the filtrate concentrated to give the free base of compound (IIc).

Suitable anion exchange resins that can be employed are strong base anion exchangers, wherein the ionic form is generally a chloride ion. Typical of such anion exchange resins are the commercially available Amberlite resins like FPA40 Cl, FPA90 Cl, FPA91 Cl, FPA97 Cl, FPA98 Cl, IRA 400, IRA402 Cl, IRA410 Cl etc.

Thus, in a typical embodiment, to a solution of the protected compound (IIa) in methanol is added a 25% aqueous solution of ammonia in water and mixture agitated at room temperature for a period of 4 to 8 hrs till completion of the deprotection. Removal of methanol by evaporation gives the free base of compound (IIc).

In another typical embodiment, an anion exchange resin, for instance, Amberlite IRA 400 is agitated with 5% aqueous sodium hydroxide at room temperature for 2 to 3 hrs and the resin filtered off. The filtered resin is washed successively with demineralised water till pH of the filtrate is in the range of 6.0 to 7.0. The resin is finally washed with a $C_{1-3}$ alcohol, for instance methanol. The hydroxy ion exchanged resin thus obtained is stirred with the protected compound (IIa) in methanol at a temperature of between 40° C. to 45° C. for 36 hours. At the end, the resin is filtered off and the filtrate concentrated to give the deprotected free base compound (IIc).

The gemcitabine free base (IIc) obtained by any of the abovementioned two methods is generally obtained as an oil and can be used as such without any purification for formation of its hydrochloride salt.

The salt formation can be effected by contacting a solution of the free base (IIc) in a $C_{1-3}$ alcohol selected from methanol, ethanol, 1-propanol and 2-propanol with hydrogen chloride for sufficient time. Both aqueous and gaseous hydrogen chloride can be employed. The hydrochloride salt thus formed can be isolated or crystallized from the same alcoholic solvent or with anyone of methanol, ethanol, 1-propanol or 2-propanol to give gemcitabine hydrochloride (IIb), generally as the β-enriched anomer having an anomeric purity >95%, most often having an anomeric purity >99%.

The anomeric and chemical purity of gemcitabine hydrochloride (IIb) thus obtained can be enriched to >99%, if necessary through one more crystallization of the same from with anyone of methanol, ethanol, 1-propanol or 2-propanol or optionally through crystallization from a mixture of water and a $C_{2-3}$ aliphatic organic acid, selected from acetic acid and propionic acid.

While all the abovementioned $C_{2-3}$ aliphatic organic acids do normally provide gemcitabine hydrochloride of formula (IIb) in high anomeric purity, acetic acid is the most preferred since it provides a compound of high chemical purity as well.

Typically, to a solution of the hydrochloride salt (IIb) in water is added acetic acid and the mixture agitated at room temperature for 10 to 12 hrs to effect crystallization. The crystallized salt (IIb) can be isolated by filtration, centrifugation or decantation and dried to give pure (IIb).

The preparation of gemcitabine hydrochloride (IIb) in high chemical and anomeric purity as per the method of the present invention is summarized in Scheme-I.

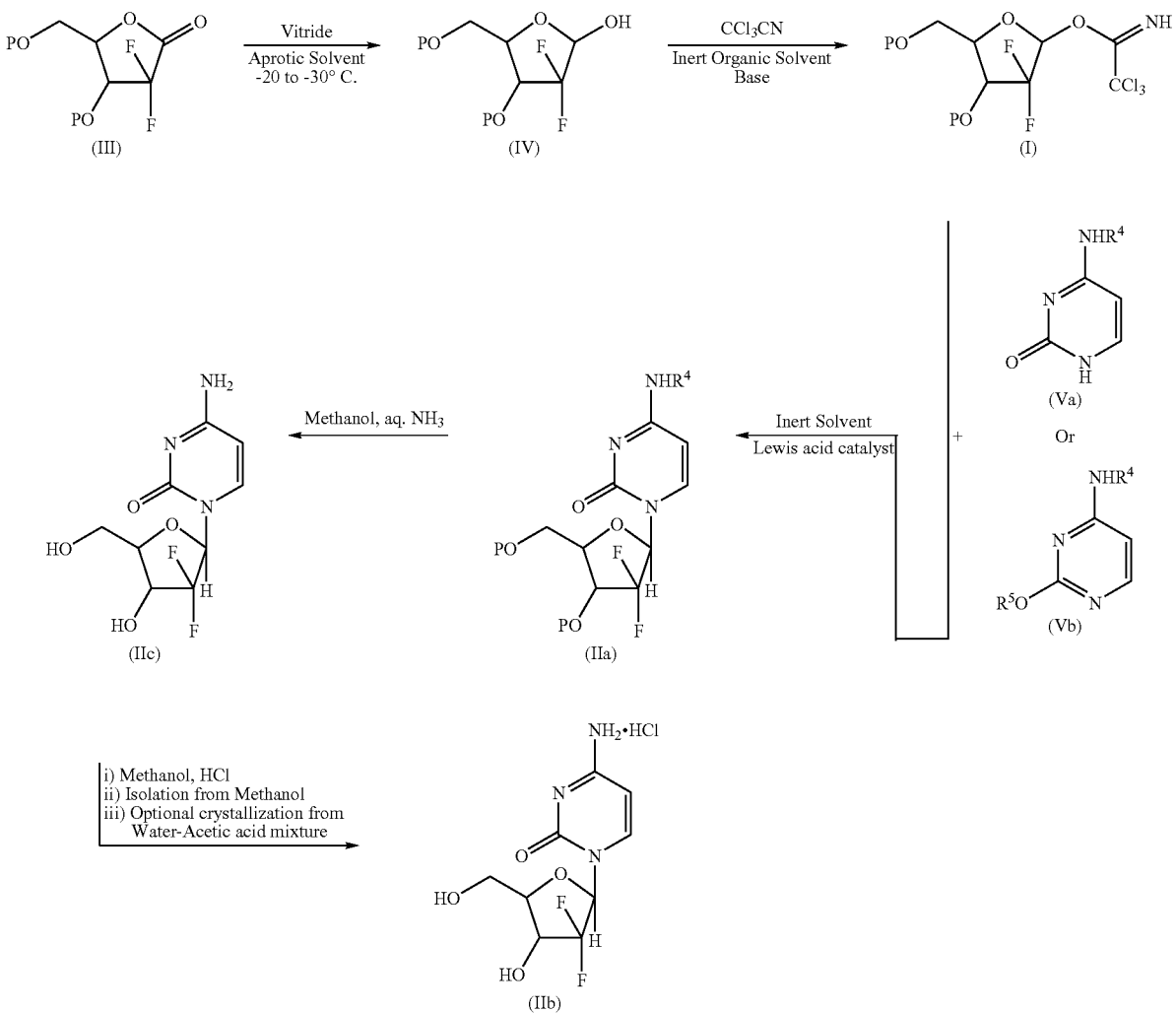

The invention can be further understood by the following examples, which in no way should be construed as to limiting the scope of the invention.

EXAMPLE-1

Preparation of $2^1$-Deoxy-$2^1,2^1$-difluoro-3,5-bisbenzoyloxy-D-ribose trichloroacetimidate (Compound of formula Ia)

Step-1: Preparation of lactol, viz. $2^1$-Deoxy-$2^1,2^1$-difluoro-D-ribofuranose-3,5-dibenzoate (Compound of formula IV)

Sodium bis(2-methoxyethoxy)aluminium hydride (Vitride; 70% in toluene; 80 ml; 0.287 mol) was added slowly to a solution of $2^1$-deoxy-$2^1,2^1$-difluoro-3,5-dibenzoate-1-oxoribose (III; 100 gm; 0.265 mol) in dry tetrahydofuran cooled to −30° C. under an atmosphere of nitrogen. After the addition, the reaction mixture was agitated at the same temperature for 1 hr and quenched by the addition of 6N hydrochloric acid. The reaction mixture was extracted with ethyl acetate. The organic layer was separated and washed with 5% sodium bicarbonate solution followed by water. Concentration of the organic layer under reduced pressure gave 100 gm (99.5%) of the title compound as an oil.

$^1$H NMR (CDCl$_3$, δ): 5.6 (m, H-1, 1H), 5.45-5.32 (br, H-3, 1H), 4.7 (m, H-4, 1H), 4.65 (br, H-5, 2H), 3.6 (s, 1H, OH).

Step-2: Preparation of $2^1$-Deoxy-$2^1,2^1$-difluoro-3,5-bisbenzoyloxy-D-ribose trichloroacetimidate (Ia)

To a mixture of trichloroacetonitrile (179.5 gm; 1.246 mol), diisopropyl ethylamine (3.73 gm; 0.028 mol), cooled to at −10 to 0° C. under an atmosphere of nitrogen was added slowly a solution of $2^1$-Deoxy-$2^1,2^1$-difluoro-D-ribofuranose-3,5-dibenzoate (Compound of formula IV obtained in Step-1; 25 gm; 0.066 mol) in 1,2-dichloroethane (50 ml). The reaction mixture was allowed to come to room temperature and stirred for further 5 hr till completion of reaction. The organic solvent was evaporated under reduced pressure to give 35 gm (100%) of the title compound as an oil.

A purified sample had the following spectroscopic characteristics. $^1$H NMR (CDCl$_3$, δ): 8.7 (s, NH, 1H), 7.36-8.1 (m, Ar, 10H), 6.51-6.59 (dd, H-1, 1H), 5.59-5.66 (dd, H-3 1H), 4.64-4.83 (m, H-5 2H, H-4 1H)

$^{13}$C NMR (CDCl$_3$, δ): 164.7-165.9 (C=NH), 127.9-130 (Ar), 121.3 (C-2), 97.58 (C-1), 90 (CCl3), 78.8 (C-4), 71.9 (C-3), 63.8 (C-5). Mass Spectrum (M$^+$): 522.3 Specific rotation +15 to +60°

EXAMPLE-2

Preparation of $2^1$-Deoxy-$2^1,2^1$-difluoro-3,5-dibenzoate-N-4-acetyl cytidine (Protected Gemcitabine, IIa)

A mixture $2^1$-Deoxy-$2^1,2^1$-difluoro-3,5-bisbenzoyloxy-D-ribose trichloroacetimidate (Ia; 5.22 g; 0.01 mol), Silylated N-acetyl cytosine (Vb; 2.45 gm; 0.016 mol w.r.t. N-Acetylcytosine) and trimethylsilyl trifluoromethane sulphonate (6.41 gm; 0.01 mol) in 1,2-dichloroethane (50 ml) was refluxed overnight. The reaction mixture was cooled to room temperature and washed with two 50 ml portions each of water followed by washing with 5% sodium bicarbonate solution and with a saturated solution of sodium chloride. Removal of dichloroethane under reduced pressure gave 5.12 gm (37%) of the title compound, a portion of it was chromatographed on silica gel.

Mass Spectrum (M$^{-1}$): 512.35

EXAMPLE-3

Preparation of $2^1$-Deoxy-$2^1,2^1$-difluoro-3,5-dibenzoate-N$^4$-acetyl cytidine (Protected Gemcitabine, IIa)

To a mixture of trichloroacetonitrile (47.6 gm; 0.33 mol), diisopropyl ethylamine (3.73 gm; 0.028 mol), cooled to −10 to 0° C. under an atmosphere of nitrogen was added slowly a solution of $2^1$-Deoxy-$2^1,2^1$-difluoro-D-ribofuranose-3,5-dibenzoate (IV; 25 gm; 0.066 mol) in 1,2-dichloroethane (50 ml). The reaction mixture was allowed to come to room temperature and stirred for further 5 hr till completion of reaction.

To the above reaction mixture containing $2^1$-Deoxy-$2^1$, $2^1$-difluoro-3,5-bisbenzoyloxy-D-ribose trichloroacetimidate (Ia; 34.5 g; 0.066 mol) in situ, was added Silylated N-acetyl cytosine (15.2 gm; 0.1 mol w.r.t. N-Acetylcytosine) and trimethylsilyl trifluoromethane sulphonate (22 gm; 0.1 mol) in 1,2-dichloromethane (300 ml) and the mixture refluxed overnight. The reaction mixture was cooled to room temperature and washed with two 100 ml portions each of water followed by washing with 5% sodium bicarbonate solution and with a saturated solution of sodium chloride. Removal of dichloroethane under reduced pressure gave 30 gm (88.7.%) of the title compound.

EXAMPLE-4

Preparation of $2^1$-Deoxy-$2^1,2^1$-difluorocytidine (Gemcitabine free base IIc)

To a solution of the protected Gemcitabine (IIa: 7 gm; obtained in Example-2 and 3) in methanol (35 ml) was added a solution of ammonium hydroxide (20%, 14 ml) and the mixture stirred at room temperature for 24 hr. Methanol was removed under reduced pressure to give the title compound as an oil.

EXAMPLE-5

Preparation of Gemcitabine Hydrochloride (IIb)

The residue obtained from Example-4 (Gemcitabine free base, IIc) was dissolved in methanol (28 ml) and decolourised with activated carbon (0.7 gm). The carbon was filtered off and to the filtrate was added Conc. hydrochloric acid (1.12 ml) and the mixture cooled to 0° C. and agitated at a temperature of 0° C. to 5° C. for 1 hr and the precipitated solid filtered and dried to give 0.56 gm (12.7%) of the title compound as a white crystalline solid. HPLC analysis showed the product to be comprising of 95% of the β-anomer.

EXAMPLE-6

Purification of Gemcitabine Hydrochloride (IIb)

The Gemcitabine hydrochloride (0.56 gm; obtained from Example-5 was dissolved in D.M water (4.5 ml) at 55-60° C.

The solution was decolourised with activated carbon (56 mg) and the carbon filtered off. The filtrate was mixed with acetic acid (45 ml) and the mixture was stirred at room temperature for 2 h. The precipitated solid was filtered and dried at 60-70° C. under vacuum for 5-6 hr to give 0.45 gm (80%) of Gemcitabine hydrochloride (IIb) having an anomeric purity of 99.94% of the β-anomer.

EXAMPLE-7

Preparation of $2^1$-Deoxy-$2^1$,$2^1$-difluorocytidine (Gemcitabine free base IIc)

Amberlite IRA 400 (100 gm; 20-25 mesh; chloride as the ionic form) was stirred with aqueous sodium hydroxide (5%; 500 ml) at room temperature for 2 to 3 hrs. The resin was filtered off and the bed washed successively with demineralised water till pH of the filtrate was in the range of 6.0 to 7.0. The resin bed was then washed with methanol and dried at room temperature.

To a solution of the protected Gemcitabine (IIa: 5.5 gm; obtained in Example-2 and 3) in methanol (50 ml) was added the hydroxy ion exchanged resin as obtained above (2.25 gm) and the mixture stirred at a temperature of 40° C. to 45° C. for 36 hrs. The resin was filtered off, washed with methanol. The filtrate was concentrated under reduced pressure to 2.0 gm (71%) of the title compound as an oil.

EXAMPLE-8

Preparation of Gemcitabine Hydrochloride (IIb)

The residue obtained from Example-7 (Gemcitabine free base, IIc) was dissolved in methanol (20 ml) and decolourised with activated carbon (0.35 gm). The carbon was filtered off and to the filtrate was added Conc. hydrochloric acid (1.0 ml) and the mixture cooled to 0° C. and agitated at a temperature of 0° C. to 5° C. for 1 hr and the precipitated solid filtered and dried to give 0.43 gm (18.9%) of the title compound as a white crystalline solid. HPLC analysis showed the product to be comprising of 95% of the β-anomer.

EXAMPLE-9

Purification of Gemcitabine Hydrochloride (IIb)

The Gemcitabine hydrochloride (0.43 gm; obtained from Example-8 was dissolved in D.M water (3.5 ml) at 55-60° C. The solution was decolourised with activated carbon (50 mg) and the carbon filtered off. The filtrate was mixed with acetic acid (34 ml) and the mixture was stirred at room temperature for 2 hrs. The precipitated solid was filtered and dried at 60-70° C. under vacuum for 5-6 hr to give 0.35 gm (81%) of Gemcitabine hydrochloride (IIb) having an anomeric purity of 99.94% of the β-anomer.

EXAMPLE-10

Preparation of 2-Deoxy-2,2-difluoro-3,5-dibenzoate-5-fluoro uridine hydrochloride salt 5-Fluorouracil (5 gm; 0.038 mol was heated with hexamethyldisilazane (13.77 gm; 0.085 mol) and catalytic amount (0.50 ml) of methanesulfonic acid in acetonitrile (15 ml) at 110-120° C. for 5-6 hrs to get a clear solution. The reaction mixture was concentrated under reduced pressure to give a gummy mass which was heated to 60° C. and mixed with a solution of $2^1$-Deoxy-$2^1$,$2^1$-difluoro-3,5-bisbenzoyloxy-D-ribose trichloroacetimidate (Ia; 6.70 gm; 0.013 mol) in acetonitrile (5 ml), followed by addition of trimethylsilyl trifluoromethane sulphonate (7.12 gm; 0.03 mol). The reaction mixture was heated under agitation at 90° C. for 10 hrs.

The reaction mixture was poured in to a mixture dichloromethane and water (100 ml; 1:1). The organic phase was separated and washed with 5% sodium bicarbonate solution, water and then evaporated to give 6.28 g (100%) of a white solid. Chromatography of the solid over silica gel using a mixture of ethyl acetate and hexane (1:1) gave 3.25 gm (51.7%) of the free base (IIa).

$^1$H NMR (CDCl$_3$, δ): 4.59 (q, 1H, H-4'), 4.68, 4.91 (dd, dd, 2H, H-5'), 5.79 (dd, 1H, H-3'), 6.52 (q, 1H, H-1'), 8.06 (d, 1H, H-6) Mass Spectrum (M$^+$): 489

The removal of the benzoyl protective group and conversion of the unprotected free base thus obtained to its hydrochloride salt was effected as per the methods described in Examples 4-9 gave 2-Deoxy-2,2-difluoro-3,5-dibenzoate-5-fluoro uridine hydrochloride salt in an anomeric purity of 70% of the β-anomer.

EXAMPLE-11

Preparation of 2-Deoxy-2,2-difluoro-3,5-dibenzoate-5-fluoro cytidine hydrochloride salt 5-Fluorocytosine (5 gm; 0.038 mol) was heated with hexamethyldisilazane (6.308 gm; 0.039 mol) and catalytic amount (0.50) of methanesulfonic at 110-120° C. for 5 to 6 hrs to get a clear solution. The temperature was brought down to 50° C. and the silylated mass mixed with a solution of $2^1$-Deoxy-$2^1$,$2^1$-difluoro-3,5-bisbenzoyloxy-D-ribose trichloroacetimidate (Ia; 6.70 gm; 0.013 mol) in acetonitrile (7 ml), followed by addition of trimethylsilyl trifluoromethane sulphonate (7.12 gm; 0.03 mol). The reaction mixture was heated under agitation at 90° C. for 10 hrs.

The reaction mixture was poured in to a mixture dichloromethane and water (100 ml; 1:1). The organic phase was separated and washed with 5% sodium bicarbonate solution, water and then evaporated to give 6.0 g of a white solid. Chromatography of the solid over silica gel using a mixture of ethyl acetate and hexane (1:1) gave 2.0 gm (31.8%) of the free base.

$^1$H NMR (CDCl$_3$, δ): 4.56 (q, 1H, H-4'), 4.73, 4.78 (dd, dd, 2H, H-5'), 5.79 (dd, 1H, H-3'), 6.63 (q, 1H, H-1'), 8.09 (d, 1H, H-6) Mass: Spectrum: 488

The removal of the benzoyl protective group and conversion of the unprotected free base thus obtained to its hydrochloride salt was effected as per the methods described in Examples 4-9 gave 2-Deoxy-2,2-difluoro-3,5-dibenzoate-5-fluoro uridine hydrochloride salt in an anomeric purity of 68% of the β-anomer.

EXAMPLE-12

Preparation of 2-Deoxy-2,2-difluoro-3,5-dibenzoate-5-thymidine hydrochloride salt Thymine (5 gm; 0.04 mol) was heated with hexamethyldisilazane (15.2 gm; 0.094 mol) and catalytic amount (0.5 ml) of trimethylsilyl chloride in acetonitrile (20 ml) at 110-120° C. for 5-6 hrs to get a clear solution. The reaction mixture was concentrated under reduced pressure to give a gummy mass which was redissolved in fresh acetonitrile (10 ml). To the solution was then added a solution of $2^1$-Deoxy-$2^1,2^1$-difluoro-3,5-bisbenzoyloxy-D-ribose trichloroacetimidate (Ia; 7.0 gm; 0.0134 mol) in acetonitrile (10 ml), followed by trimethylsilyl trifluoromethane sulphonate (7.37 gm; 0.033 mol). The reaction mixture was heated under agitation at 90 C for 5 hrs.

The reaction mixture was poured in to a mixture dichloromethane and water (100 ml; 1:1). The organic phase was separated and washed with 5% sodium bicarbonate solution, water and then evaporated to give 6.0 gm of a white solid, which was chromatographed over silica gel using a mixture of ethyl acetate and hexane.

Mass Spectrum: 485

The removal of the benzoyl protective group and conversion of the unprotected free base thus obtained to its hydrochloride salt was effected as per the methods described in Examples 4-9 gave 2-Deoxy-2,2-difluoro-3,5-dibenzoate-5-fluoro uridine hydrochloride salt in an anomeric purity of 70% of the β-anomer.

EXAMPLE-13

Preparation of 2-Deoxy-2,2-difluoro-3,5-dibenzoate-uridine hydrochloride salt

Uracil (5 gm; 0.044 mol) was heated with hexamethyldisilazane (76.8. gm; 0.47 mol) and of trimethylsilyl chloride (40 ml) at 135-140° C. for 5-6 hrs to get a clear solution. The reaction mixture was concentrated under reduced pressure to give a gummy mass, which was redissolved in fresh acetonitrile (20 ml). To the solution was then added a solution of $2^1$-Deoxy-$2^1,2^1$-difluoro-3,5-bisbenzoyloxy-D-ribose trichloroacetimidate (Ia; 7.5 gm; 0.0143 mol) in acetonitrile (50 ml), followed by trimethylsilyl trifluoromethane sulphonate (10.43 gm; 0.047 mol). The reaction mixture was heated under agitation at 90° C. for 10 hrs.

The reaction mixture was poured in to a mixture dichloromethane and water (100 ml; 1:1). The organic phase was separated and washed with 5% sodium bicarbonate solution, water and then evaporated to give 6.5 gm of a white solid, which was chromatographed over silica gel using a mixture of ethyl acetate and hexane.

Mass Spectrum: $M^{-1}$: 472.5

The removal of the benzoyl protective group and conversion of the unprotected free base thus obtained to its hydrochloride salt was effected as per the methods described in Examples 4-9 gave 2-Deoxy-2,2-difluoro-3,5-dibenzoate-5-fluoro uridine hydrochloride salt in an anomeric purity of 65% of the β-anomer.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

We claim:
1. A compound of formula (I):

wherein,
P is hydrogen or a hydroxy protective group.

2. The compound of claim 1, wherein P is selected from the group of formyl, 2-chloroacetyl, benzyl, diphenylmethyl, triphenyl methyl, 4-nitrobenzyl, phenoxycarbonyl, tertiary butyl, methoxymethyl, tetyrahydropyranyl, allyl, tetrahydrothienyl, 2-methoxethoxy methyl, methoxy acetyl, phenoxy acetyl, isobutyryl, ethoxy carbonyl, benzyloxy carbonyl, mesyl, trimethylsilyl, isopropyl dimethylsilyl, methyldiisopropyl silyl, triisopropyl silyl, or tertiary butyldimethyl silyl.

3. A process for preparing a compound of formula (I):

wherein,
P is hydrogen or a hydroxy protective group;
the method comprising:
contacting a compound of formula (IV):

wherein P is as defined hereinbefore, with trichloroacetonitrile, in an inert organic solvent and in the presence of a base.

4. The process of claim 3, wherein the organic solvent is selected from the group of halogenated hydrocarbons, acetic acid, $(C_{1-4})$ alkyl esters, ethers, aromatic hydrocarbons, and combinations thereof.

5. The process of claim 3, wherein the inert organic organic solvent is selected from the group of dichloromethane, 1,2-dichloroethane, ethyl acetate, diisopropylether, toluene, and combinations thereof.

6. The process of claim 3, wherein the base is selected from the group of diethylamine, triethylamine, diisopropylethylamine, cyclohexylamine, pyridine, 2,4-dimethylamino pyridine, N-methyl morpholine, and combinations thereof.

7. The process of claim 3, wherein the base is employed in catalytic, equimolar or in molar proportions of about 1 to about 3 moles per mole of the compound of formula (IV).

8. The process of claim 3, wherein the trichloroacetonitrile is employed in equimolar proportions to the compound of formula (IV), in molar proportions of about 1 to about 20 moles per mole of the compound of formula (IV), or in molar proportions of about 1.0 to about 15 moles per mole of the compound of formula (IV).

9. The process of claim 3, wherein the contacting is carried out at a temperature of about −20° C. to about 20° C.

10. A stereoselective glycosylation process for the preparation of greater than about 99% β-enriched anomer of gemcitabine hydrochloride formula (IIb):

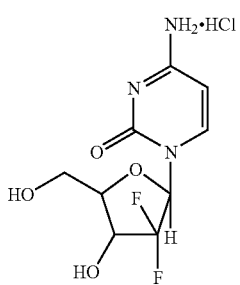

comprising the steps of:
a) contacting a compound of formula (I),

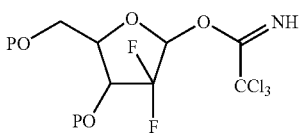

wherein P is as defined hereinbefore, with a cytosine of formula (Va) or (Vb),

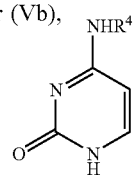

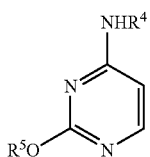

wherein $R^4$ is a nitrogen protective group, and $R^5$ is a hydroxy protective group, in the presence of an inert organic solvent and optionally in the presence of a Lewis acid catalyst to produce protected gemcitabine free base of formula (IIa),

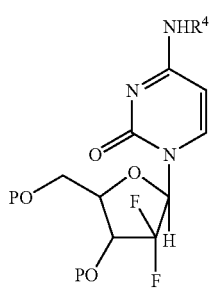

wherein P and $R^4$ are as defined hereinbefore;

b) removing the protective groups by treating the compound of formula (IIa) with aqueous ammonia in the presence of a $C_{1-3}$ alcohol or with hydroxy ion exchanged anion exchange resins, to give the β-enriched anomer of gemcitabine free base of formula (IIc);

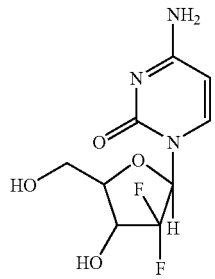

c) contacting the gemcitabine free base of formula (IIc) with hydrogen chloride in a $C_{1-3}$ alcohol to give the β-enriched anomer of gemcitabine hydrochloride of formula (IIb) in a yield of at least about 95% and optionally a purity of at least about 95%; and d) optionally further enriching the β-anomer content of gemcitabine hydrochloride of formula (IIb) to greater than about 99% through crystallization from a mixture of a $C_{2-3}$ aliphatic organic acid and water.

11. The process of claim 10, wherein the nitrogen protective group $R^4$ and the hydroxyl group $R^5$ in the compounds of formula (Va) and (Vb) are acetyl or trialkylsilyl.

12. The process of claim 10, wherein the inert organic solvent is selected from the group of acetonitrile, toluene, xylene and its isomers, chlorobenzene, ortho-dichlorobenzene, dichloromethane, 1,1-dichloroethane, 1,2-dichloroethane, 1,1,2-trichloroethane, anisole, and combinations thereof.

13. The process of claim 10, wherein the Lewis acid catalyst is tin tetrachloride, trimethylsilyltrifluoromethanesulphonate, trimethylsilyl nonafluorobutylsulphonate, trimethylsilyl perchlorate, boron trifluoride diethyletherate, or trimethylsilyl tetrafluoroborate.

14. The process of claim 10, wherein the compounds (Va) and (Vb) are employed in molar proportions of about 1 to about 2.0 moles per mole of compound of formula (I).

15. The process of claim 10, wherein the $C_{1-3}$ alcohol is selected from the group of methanol, ethanol, 1-propanol, 2-propanol, and combinations thereof.

16. The process of claim 10, wherein the deprotection of protective groups, P, $R^4$, and $R^5$ comprises contacting the compound of formula (IIa) with aqueous ammonia in the presence of a $C_{1-3}$ alcohol at a temperature of between ambient to a temperature of about 60° C.

17. The process of claim 10, wherein the anion exchange resin is a strong base anion exchange resin.

18. The process of claim 10, wherein the strong base anion exchange resin is an Amberlite resin.

19. The process of claim 18, wherein the Amberlite resin is selected from the group of FPA40 Cl, FPA90 Cl, FPA91 Cl, FPA97 Cl, FPA98 Cl, IRA 400, IRA402 Cl, and IRA410 Cl.

20. The process of claim 10, wherein the $C_{2-3}$ aliphatic organic acid is acetic acid, propionic acid, or a combination thereof.

* * * * *

UNITED STATES PATENT AND TRADEMARK OFFICE
CERTIFICATE OF CORRECTION

PATENT NO. : 7,235,647 B2  Page 1 of 1
APPLICATION NO. : 11/332830
DATED : June 26, 2007
INVENTOR(S) : Maikap et al.

It is certified that error appears in the above-identified patent and that said Letters Patent is hereby corrected as shown below:

On the title page, item (54), in column 1, line 3, delete "21-DEOXY,21,21-DIFLUORO" and insert -- $2^1$-DEOXY,$2^1$,$2^1$-DIFLUORO --, therefor.

On the title page, item (56), under "Other Publications", in column 2, line 4, delete "fo" and insert -- for --, therefor.

On the title page, item (57), under "Abstract", in column 2, line 5, delete "slats" and insert -- salts --, therefor.

In column 1, line 3, delete "21-DEOXY,21,21-DIFLUORO" and insert -- $2^1$-DEOXY,$2^1$,$2^1$-DIFLUORO --, therefor.

In column 36, line 17, in Claim 2, delete "tetyrahydropyranyl" and insert -- tetrahydropyranyl --, therefor.

In column 36, line 54 (Approx.), in Claim 5, before "solvent" delete "organic".

Signed and Sealed this

Fifth Day of August, 2008

JON W. DUDAS
*Director of the United States Patent and Trademark Office*